US006787335B2

(12) United States Patent
Salceda et al.

(10) Patent No.: US 6,787,335 B2
(45) Date of Patent: Sep. 7, 2004

(54) COMPOSITIONS AND METHODS OF DIAGNOSING, MONITORING, STAGING, IMAGING AND TREATING MAMMARY GLAND CANCER

(75) Inventors: Susana Salceda, San Jose, CA (US); Ping Hu, San Ramon, CA (US); Herve Recipon, San Francisco, CA (US); Robert Cafferkey, South San Francisco, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/817,318

(22) Filed: Mar. 26, 2001

(65) Prior Publication Data

US 2002/0037250 A1 Mar. 28, 2002

Related U.S. Application Data

(60) Provisional application No. 60/192,277, filed on Mar. 27, 2000.

(51) Int. Cl.[7] .................................................. C12P 21/06
(52) U.S. Cl. ................. 435/69.1; 435/252.3; 435/320.1; 435/325; 536/23.1; 536/23.5
(58) Field of Search .............................. 536/23.1, 23.5; 435/69.1, 320.1, 252.3, 325

(56) References Cited

U.S. PATENT DOCUMENTS

| 4,889,806 A | * 12/1989 | Olson et al. ............. 435/172.3 |
| 4,946,778 A | 8/1990 | Ladner et al. ............. 435/69.6 |
| 5,837,468 A | * 11/1998 | Wang et al. ................... 435/6 |

FOREIGN PATENT DOCUMENTS

| WO | WO 99/57565 A2 | 11/1999 |
| WO | WO 01/72780 A2 | 10/2001 |

OTHER PUBLICATIONS

Burgess et al. Journal of Cell Biology, 1990, 11: 2129–2138.*
Lazar et al. Molecular and Cell Biology, 1988, 8: 1247–1252.*
Tao. et al. The Journal of Immunology, 1989, 143(8): 2595–2601.*
Gillies et al. Human Antibodies and Hybridomas, 1990, 1(1): 47–54.*
Jansen, M et al, 1995, Pediatric Res, 37 (6): 681–686.*
Alberts et al. Molecular Biology of the Cell, 3rd edition, 1994, p. 465.*
Shantz and Pegg. Int J of Biochem and Cell Biol., 1999, vol. 31, pp. 107–122.*
McClean and Hill. Eur J of Cancer, 1993, vol. 29A, pp. 2243–2248.*
Fu et al. EMBO Journal, 1996, vol. 15, pp. 4392–4401.*
Yokota, J et al. Oncogene, 1988,vol. 3, pp. 471–475.*
Ezzell. J. NIH Res, 1995, 7:46–49.*
Spitler. Cancer Biotherapy, 1995, 10:1–3.*
Boon. (Adv Can Res, 1992, 58:177–210.*
Miller. 1995, FASEB J., vol. 9, pp. 190–199.*
Deonarain. 1998, Expert Opin. Ther. Pat., vol. 8, pp. 53–69.*
Verma. Sep. 1997, Nature, vol. 389, pp. 239–242.*
Crystal. 1995, Science, vol. 270, p. 404–410.*
Sambrook et al, 1989 (Molecular Cloning, A Laboratory Manual, 2nd Edition, Cold Spring Harbor Press, Cold Spring Harbor, p. 16.3–16.4.*
MPSRCH search report, 2002, pp. 4–5.*
Cole et al., "The EBV–Hybridoma Technique and Its Application to Human Lung Cancer", *Monoclonal Antibodies and Cancer Therapy*, pp. 77–96, Alan R. Liss, Inc. 1985.
Coligan et al., *Current Protocols in Immunology* 1(2):Chapter 5 1991.
Cooney et al., "Site–Specific Oligonucleotide Binding Represses Transcription of the Human c–myc Gene in Vitro", Science 1988 241:456.
Beal and Dervan et al., "Second Structural Motif for Recognition of DNA by Oligonucleotide–Directed Triple–Helix Formation", *Science* 1991 251:1360.
Chapter 20, *Gene Therapy and other Molecular Genetic–based Therapeutic Approaches*, Human Molecular Genetics, T Strachan and A P Read, BIOS Scientific Publishers Ltd 1996.
Diatchenko et al., "Suppression subtractive hybridization:A method for generating differentially regulated or tissue–specific cDNA probes and libraries", *Proc. Natl. Acad. Sci. USA* 93:6025–6030 1996.
Gluzman et al., "SV40–Transformed Simian Cells Support the Replication of Early SV40 Mutants", *Cell* 23:175 1981.
Griffin et al., "Initial Clinical Study of Indium–111–Labeled Clone 110 Anticarcinoembryonic Antigen Antibody in Patients With Colorectal Cancer", *J. Clin. Onc.* 1991 9:631–640.
Kohler et al., "Continuous cultures of fused cells secreting antibody of predefined specificity", *Nature* 1975 256:495–497.
Kozbor et al., "The production of monoclonal antibodies from human lymphocytes", *Immunology Today* 1983 4:72.
Lauffer R.B., "Targeted Relaxation Enhancement Agents for MRI*", *Magnetic Resonance in Medicine* 1991 22:339–342.
Lee et al., "Complexes formed by (pyrimidine)$_n$ (purine)$_n$ DNAs on lowering the pH are three–stranded", *Nucleic Acids Res* 1979 6:3073.

(List continued on next page.)

*Primary Examiner*—Susan Ungar
*Assistant Examiner*—Minh-Tam Davis
(74) *Attorney, Agent, or Firm*—Licata & Tyrrell P.C.

(57) ABSTRACT

The present invention provides polynucleotides and polypeptides which are diagnostic markers for mammary gland cancer. In addition, antibodies immunospecific for these markers are provided. Vectors, hosts cells and methods for producing these markers, as well as methods and tools for using these markers in detecting, diagnosing, monitoring, staging, prognosticating, imaging and treating mammary gland cancer are also provided.

6 Claims, No Drawings

OTHER PUBLICATIONS

O'Connor, *J. Neurochem* 1991 56:560 in *Oligodeoxynucleotides as Antisense Inhibitors of Gene Expression*, CRC Press, Boca Raton, FL 1988.

Rattan et al., "Aging and Cellular Defense Mechanisms", *Protein Synthesis: Posttranslational Modifications and Aging, Ann. N.Y. Acad. Sci.* 663: 48–62 1992.

Sumerdon et al., "An Optimized Antibody–Chelator Conjugate for Imaging of Carcinoembryonic Antigen with Indium–111", *Nucl. Med. Biol.* 1990 17:247–254.

Carmeci et al. Identification of a gene (GRP30) with homology to the G–protein–coupled receptor superfamily associated with estrogen receptor expression in breast cancer, Genomics, 1997; vol. 45:607–617.

Schorr et al. Bcl–2 gene family and related proteins in mammary gland involution and breast cancer, J. Mammary Gland Bio. And Neo.. 1999; vol. 4(2):153–164.

Database Genebank, Accession No. AL356432, Wilson et al., Human DNA sequence from clone RP11–325024 on chromosome 6, complete sequence, Feb. 2, 2001, see sequence.

\* cited by examiner

COMPOSITIONS AND METHODS OF DIAGNOSING, MONITORING, STAGING, IMAGING AND TREATING MAMMARY GLAND CANCER

INTRODUCTION

This application claims the benefit of U.S. Provisional Application Serial No. 60/192,277, filed Mar. 27, 2000.

FIELD OF THE INVENTION

This invention relates, in part, to newly identified polynucleotides and polypeptides encoded thereby, as well as methods for producing and using these polynucleotides and polypeptides. Antibodies which are immunospecific for these polypeptides are also described. Expression of the newly identified polynucleotides and levels of the polypeptides encoded thereby are upregulated in or specific to mammary gland cancer tissue. These new polynucleotides and polypeptides, referred to herein as Mammary Gland Cancer Specific Genes or MSGs are believed to be useful in assays for detecting, diagnosing, monitoring, staging, prognosticating, imaging and treating cancers, particularly mammary gland cancer.

BACKGROUND OF THE INVENTION

It is estimated that one out of every nine women in America will develop mammary gland cancer sometime during her life based on a lifespan of 85 years. Annually, over 180,000 women in the United States are diagnosed with mammary gland cancer and approximately 46,000 die from this disease. Every woman is at risk for mammary gland cancer. However, a woman's chances of developing this cancer increase as she grows older; 80 percent of all cancers are found in women over the age of 50. There are also several risk factors that can increase a woman's chances of developing mammary gland cancer. These include a family history of mammary gland cancer, having no children or the first child after the age of 30, and an early start of menstruation. However, more than 70 percent of women who develop mammary gland cancer have no known risk factors. Less than 10 percent of mammary gland cancer cases are thought to be related to the BRCA1 gene discovered in 1994. Researchers are now investigating the role of other factors such as nutrition, alcohol, exercise, smoking, and oral contraceptives in development of this gynecologic cancer. Mammograms, or special x-rays of the breast, can detect more than 90 percent of all cancers.

Procedures used for detecting, diagnosing, monitoring, staging, and prognosticating mammary gland cancer are of critical importance to the outcome of the patient. Patients diagnosed early generally have a much greater five-year survival rate as compared to the survival rate for patients diagnosed with distant metastasized mammary gland cancer. New diagnostic methods which are more sensitive and specific for detecting early mammary gland cancer are clearly needed.

Cancer patients are closely monitored following initial therapy and during adjuvant therapy to determine response to therapy and to detect persistent or recurrent disease or metastasis. Thus, there is also clearly a need for cancer markers which are more sensitive and specific in detecting mammary gland cancer recurrence.

Another important step in managing mammary gland cancer is to determine the stage of the patient's disease. Stage determination has potential prognostic value and provides criteria for designing optimal therapy. Generally, pathological staging of cancer is preferable over clinical staging because the former gives a more accurate prognosis. However, clinical staging would be preferred were it at least as accurate as pathological staging because it does not depend on an invasive procedure to obtain tissue for pathological evaluation. Staging of cancer would be improved by detecting new markers in cells, tissues or bodily fluids which could differentiate between different stages of invasion.

The present invention relates to newly identified polynucleotides and polypeptides encoded thereby which are referred to herein as Mammary Gland Cancer Specific Genes or MSGs, as well as antibodies which are immunospecific for the polypeptides. The present invention also relates to methods for use of these MSGs in detecting, diagnosing, monitoring, staging, prognosticating, imaging and treating mammary gland cancer. For purposes of the present invention, MSG refers, among other things, to native protein expressed by the gene comprising a polynucleotide sequence of SEQ ID NO: 1, 2, 3, 4, 5, 6, 7, 8, 9, 10, 11, 12, 13, 14, 15, 16, 17, 18, 19 or 20. By MSG it is also meant herein polynucleotides which, due to degeneracy in genetic coding, comprise variations in nucleotide sequence as compared to SEQ ID NO: 1, 2, 3, 4, 5, 6, 7, 8, 9, 10, 11, 12, 13, 14, 15, 16, 17, 18, 19 or 20, but which still encode the same protein. In the alternative, what is meant by MSG as used herein, means the native mRNA encoded by the gene comprising the polynucleotide sequence of SEQ ID NO: 1, 2, 3, 4, 5, 6, 7, 8, 9, 10, 11, 12, 13, 14, 15, 16, 17, 18, 19 or 20, or a polynucleotide which is capable of hybridizing under stringent conditions to the antisense sequence of SEQ ID NO: 1, 2, 3, 4, 5, 6, 7, 8, 9, 10, 11, 12, 13, 14, 15, 16, 17, 18, 19 or 20.

Other objects, features, advantages and aspects of the present invention will become apparent to those of skill in the art from the following description. It should be understood, however, that the following description and the specific examples, while indicating preferred embodiments of the invention are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide isolated polynucleotide sequences comprising SEQ ID NO: 1, 2, 3, 4, 5, 6, 7, 8, 9, 10, 11, 12, 13, 14, 15, 16, 17, 18, 19 or 20; fragments or portions of such sequences which contain at least 15 contiguous nucleobases of SEQ ID NO: 1, 2, 3, 4, 5, 6, 7, 8, 9, 10, 11, 12, 13, 14, 15, 16, 17, 18, 19 or 20; nucleic acid sequences which, due to degeneracy in genetic coding, comprise variations in polynucleotide sequence as compared to SEQ ID NO: 1, 2, 3, 4, 5, 6, 7, 8, 9, 10, 11, 12, 13, 14, 15, 16, 17, 18, 19 or 20, but which still encode the same protein; and nucleic acid sequences which are capable of hybridizing under stringent conditions to the antisense sequence of SEQ ID NO: 1, 2, 3, 4, 5, 6, 7, 8, 9, 10, 11, 12, 13, 14, 15, 16, 17, 18, 19 or 20. The present invention further relates to isolated polypeptides encoded by the above-described polynucleotides. These polynucleotides and/or the polypeptides encoded thereby are referred to generally herein as Mammary Gland Cancer Specific Genes or MSGs.

It is another object of the present invention to provide vectors containing the MSG polynucleotides and host cells for expression and recovery of the MSG polypeptides encoded thereby.

It is another object of the present invention to provide antibodies which are immunospecific for MSG polypeptides.

It is another object of the present invention to provide tools for detection of MSGs. Such tools include, but are not limited to, antisense oligonucleotides which specifically hybridize with the MSGs and antibodies which are immunospecific for the MSGs.

It is another object of the present invention to provide a method for diagnosing the presence of mammary gland cancer by analyzing for changes in levels of MSG in cells, tissues or bodily fluids compared with levels of MSG in preferably the same cells, tissues, or bodily fluid type of a normal human control, wherein a change in levels of MSG in the patient versus the normal human control is associated with mammary gland cancer.

Further provided is a method of diagnosing metastatic cancer in a patient having mammary gland cancer which is not known to have metastasized by identifying a human patient suspected of having mammary gland cancer that has metastasized; analyzing a sample of cells, tissues, or bodily fluid from such patient for MSG; comparing the MSG levels in such cells, tissues, or bodily fluid with levels of MSG in preferably the same cells, tissues, or bodily fluid type of a normal human control, wherein an increase in MSG levels in the patient versus the normal human control is associated with mammary gland cancer which has metastasized.

Also provided by the invention is a method of staging mammary gland cancer in a human which has such cancer by identifying a human patient having such cancer; analyzing a sample of cells, tissues, or bodily fluid from such patient for MSG; comparing MSG levels in such cells, tissues, or bodily fluid with levels of MSG in preferably the same cells, tissues, or bodily fluid type of a normal human control sample, wherein an increase in MSG levels in the patient versus the normal human control is associated with a cancer which is progressing and a decrease in the levels of MSG is associated with a cancer which is regressing or in remission.

Further provided is a method of monitoring mammary gland cancer in a human having such cancer for the onset of metastasis. The method comprises identifying a human patient having such cancer that is not known to have metastasized; periodically analyzing a sample of cells, tissues, or bodily fluid from such patient for MSG; comparing the MSG levels in such cells, tissue, or bodily fluid with levels of MSG in preferably the same cells, tissues, or bodily fluid type of a normal human control sample, wherein an increase in MSG levels in the patient versus the normal human control is associated with a cancer which has metastasized.

Further provided is a method of monitoring the change in stage of mammary gland cancer in a human having such cancer by looking at levels of MSG in a human having such cancer. The method comprises identifying a human patient having such cancer; periodically analyzing a sample of cells, tissues, or bodily fluid from such patient for MSG; comparing the MSG levels in such cells, tissue, or bodily fluid with levels of MSG in preferably the same cells, tissues, or bodily fluid type of a normal human control sample, wherein an increase in MSG levels in the patient versus the normal human control is associated with a cancer which is progressing and a decrease in the levels of MSG is associated with a cancer which is regressing or in remission.

Further provided are new therapeutic agents and methods of identifying therapeutic agents targeted to MSGs for use in imaging and treating disease relating to MSGs such as mammary gland cancer. For example, in one embodiment, therapeutic agents such as antibodies targeted against MSG or fragments of such antibodies can be used to detect or image localization of MSG in a patient for the purpose of detecting or diagnosing a disease or condition. Such antibodies can be polyclonal, monoclonal, or omniclonal or prepared by molecular biology techniques. The term "antibody", as used herein and throughout the instant specification, is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. Therapeutic agents such as small molecules or antibodies or fragments thereof which decrease the concentration and/or activity of MSG can also be used in the treatment of diseases characterized by expression of MSG. In these applications, the antibody can be used without or with derivatization to a cytotoxic agent such as a radioisotope, enzyme, toxin, drug or a prodrug. Therapeutic agents of the present invention also include agonists and antagonists of MSG polypeptides and vaccines capable of inducing an immune response against MSG polypeptides. Such agents can be readily identified in accordance with the teachings herein.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

GLOSSARY

The following illustrative explanations are provided to facilitate understanding of certain terms used frequently herein. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 µg of plasmid or DNA fragment is digested with about 2 units of enzyme in about 20 µl of reaction buffer. For the purpose of isolating DNA fragments for plasmid construction, typically 5 to 50 µg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

ISOLATED means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. When introduced into host cells in culture or in whole organisms, such DNAs still would be isolated, as the term is used herein, because they would not be in their naturally occurring form or environment. Similarly, the polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

LIGATION refers to the process of forming phosphodiester bonds between two or more polynucleotides, which most often are double-stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below.

OLIGONUCLEOTIDE(S) refers to relatively short polynucleotides of about 8 to about 50 nucleobases. Often the term refers to single-stranded deoxyribonucleotides, but it can refer as well to single- or double-stranded ribonucleotides, RNA:DNA hybrids and double-stranded DNAS, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

PLASMIDS generally are designated herein by a lower case "p" preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in voluminous research literature, and they are well known to those of skill in the art.

Known modifications which may be present in polypeptides of the present invention include, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing events and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same post-translational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

A variant may comprise a polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

A variant may also comprise a polypeptide that differs in amino acid sequence from another, reference polypeptide. Generally, differences are limited so that the sequences of the reference and the variant are closely similar overall and, in many regions, identical.

A variant and reference polypeptide may differ in amino acid sequence by one or more substitutions, additions, deletions, fusions and truncations, which may be present in any combination.

RECEPTOR MOLECULE, as used herein, refers to molecules which bind or interact specifically with MSG polypeptides of the present invention and is inclusive not only of classic receptors, which are preferred, but also other molecules that specifically bind to or interact with polypeptides of the invention (which also may be referred to as "binding molecules" and "interaction molecules," respectively and as "MSG binding or interaction molecules". Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Receptors also may be non-naturally occurring, such as antibodies and antibody-derived reagents that bind to polypeptides of the invention.

DETAILED DESCRIPTION OF THE INVENTION

Polynucleotides and Polypeptides

The present invention relates to newly identified isolated polynucleotides and polypeptides encoded thereby which are upregulated in or specific to mammary gland cancer tissue. These polynucleotides and the polypeptides encoded thereby are believed to be useful as diagnostic markers for cancer, and in particular mammary gland cancer. The polynucleotides and polypeptides are also useful in the development of imaging agents and therapeutic agents for cancer, and in particular mammary gland cancer.

For purposes of the present invention, by polynucleotides it is meant to include isolated nucleic acid sequences comprising single- and double-stranded DNA, DNA that is a mixture of single- and double-stranded regions, single and double-stranded RNA or hybrids thereof wherein the sequences comprise SEQ ID NO: 1, 2, 3, 4, 5, 6, 7, 8, 9, 10, 11, 12, 13, 14, 15, 16, 17, 18, 19 or 20, fragments of at least 15 contiguous nucleobases of SEQ ID NO: 1, 2, 3, 4, 5, 6, 7, 8, 9, 10, 11, 12, 13, 14, 15, 16, 17, 18, 19 or 20, nucleic acid sequences which, due to degeneracy in genetic coding, comprise variations in polynucleotide sequence as compared to SEQ ID NO: 1, 2, 3, 4, 5, 6, 7, 8, 9, 10, 11, 12, 13, 14, 15, 16, 17, 18, 19 or 20, but which still encode the same protein, and nucleic acid sequences which are capable of hybridizing under stringent conditions to the antisense sequence of SEQ ID NO: 1, 2, 3, 4, 5, 6, 7, 8, 9, 10, 11, 12, 13, 14, 15, 16, 17, 18, 19 or 20. By stringent conditions it is meant that hybridization will occur only if there is at least 95%, and more preferably at least 97% identity between the sequences. RNA sequences may be in the form of mRNA while DNA sequences may be in the form of cDNA or genomic DNA obtained by cloning or produced by chemical synthetic techniques or by a combination thereof. As used herein, the term polynucleotide also includes DNAs or RNAs, as described above, that contain one or more modified bases. Examples of modified bases include, but are not limited to, backbone modifications to increase stability and incorporation of unusual bases such as inosine or tritylated bases.

For purposes of the present invention, by polypeptides it is meant to include the recombinant, natural and synthetic polypeptides with amino acid sequences encoded by the polynucleotides of SEQ ID NO: 1, 2, 3, 4, 5, 6, 7, 8, 9, 10, 11, 12, 13, 14, 15, 16, 17, 18, 19 or 20, or fragments or variants thereof with similar activities and/or levels in cancerous tissues to the amino acid sequences encoded by the polynucleotides of the present invention. Among preferred variants are those that vary from the polypeptides encoded by SEQ ID NO: 1, 2, 3, 4, 5, 6, 7, 8, 9, 10, 11, 12, 13, 14, 15, 16, 17, 18, 19 or 20 by conservative amino acid substitutions. conservative amino acid substitutions typically include replacement, one for another, of the aliphatic amino acids such as Ala, Val, Leu and Ile, the hydroxyl residues Ser and Thr, the acidic residues Asp and Glu, the amide residues Asn and Gln, the basic residues Lys and Arg, and the aromatic residues Phe and Tyr.

Using suppression subtractive hybridization, it has now been found that these polynucleotides, and the polypeptides encoded thereby, are upregulated in, or specific to, mammary gland cancer tissue. Thus, it is believed that these polynucleotides and polypeptides, also referred to herein as Mammary Gland Cancer Specific Genes or MSGs, are useful as diagnostic markers for mammary gland cancer, as well as otherwise described herein.

Fragments

Also among preferred embodiments of this aspect of the present invention are polypeptides comprising fragments of MSGs, and fragments of variants and derivatives of the MSGs.

In this regard a fragment is a polypeptide having an amino acid sequence that entirely is the same as part but not all of the amino acid sequences encoded by the MSGs of SEQ ID NO: 1, 2, 3, 4, 5, 6, 7, 8, 9, 10, 11, 12, 13, 14, 15, 16, 17, 18, 19 or 20 and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a MSG polypeptide of the present comprised within a precursor polypeptide designed for expression in a host and having heterologous pre- and pro-polypeptide regions fused to the amino terminus of the MSG fragment and an additional region fused to the carboxyl terminus of the fragment. Therefore, fragments in one aspect of the meaning intended herein, refers to the portion or portions of a fusion polypeptide or fusion protein derived from a MSG of the present invention.

As representative examples of polypeptide fragments of the invention, there may be mentioned those which have from about 15 to about 139 amino acids.

In this context "about" includes the particularly recited range and ranges larger or smaller by several, a few, 5, 4, 3, 2 or 1 amino acid at either extreme or at both extremes. Highly preferred in this regard are the recited ranges plus or minus as many as 5 amino acids at either or at both extremes. Particularly highly preferred are the recited ranges plus or minus as many as 3 amino acids at either or at both the recited extremes. Especially preferred are ranges plus or minus 1 amino acid at either or at both extremes or the recited ranges with no additions or deletions. Most highly preferred of all in this regard are fragments from about 15 to about 45 amino acids.

Among especially preferred fragments of the invention are truncation mutants of the MSGs. Truncation mutants include MSG polypeptides encoded by SEQ ID NO: 1, 2, 3, 4, 5, 6, 7, 8, 9, 10, 11, 12, 13, 14, 15, 16, 17, 18, 19, or 20, or variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out above also are preferred embodiments of truncation fragments, which are especially preferred among fragments generally.

Also preferred in this aspect of the invention are fragments characterized by structural or functional attributes of the MSGs. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of MSGs. Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions are particularly preferred. Among highly preferred fragments in this regard are those that comprise regions of MSGs that combine several structural features, such as several of the features set out above. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of MSGs. Most highly preferred in this regard are fragments that have a chemical, biological or other activity of a MSG, including those with a similar activity or an improved activity, or with a decreased undesirable activity. Highly preferred in this regard are fragments that contain regions that are homologs in sequence, or in position, or in both sequence and to active regions of related polypeptides, and which include mammary gland specific-binding proteins. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques. In accordance with this aspect of the invention the vector may be, for example, a plasmid vector, a single- or double-stranded phage vector, or a single- or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts for a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are PWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* laci and lacZ and promoters, the T3 and T7 promoters, the gpt promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of *E. coli* and the trpl gene of *S. cerevisiae*.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. A region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium*. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322. Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., Cell 23: 175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The MSG polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

MSG polynucleotides and polypeptides may be used in accordance with the present invention for a variety of applications, particularly those that make use of the chemical and biological properties of the MSGs. Additional applications relate to diagnosis and to treatment of disorders of cells, tissues and organisms. These aspects of the invention are illustrated further by the following discussion.

Antibodies

The MSG polypeptides of the invention or their fragments or variants thereof, or cells expressing them can be used as immunogens to produce antibodies immunospecific for the MSG polypeptides. The term "immunospecific" means that the antibodies have substantially greater affinity for the polypeptides of the invention than their affinity for other related polypeptides in the prior art. These antibodies can be polyclonal or monoclonal. In addition, by the term "antibody" it is meant to include chimeric, single chain and humanized and fully human antibodies as well as Fab fragments or products of Fab expression libraries.

Antibodies generated against the MSG polypeptides can be obtained by administering the polypeptides or epitope-bearing fragments, variants or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, can be used to express humanized antibodies.

The above-described antibodies can be used to isolate or to identify clones expressing the polypeptide or to purify the polypeptides by affinity chromatography.

Antibodies against MSG polypeptides can also be used to treat mammary gland cancer, among others.

Diagnostic Tools

The present invention also relates to diagnostic tools such as antibodies which are immunospecific for MSGs or labeled oligonucleotide probes which hybridize to MSGs.

Antibodies immunospecific for MSGs are described in detail in the preceding section.

Antisense oligonucleotides which hybridize to a portion of a polynucleotide of the present invention can be chemically synthesized via an automated oligonucleotide synthesizer or produced via alternative methods such as in vitro recombinant DNA-mediated techniques and by expression of DNA in cells and organisms. Most often oligonucleotides comprise single-stranded deoxyribonucleotides. However, oligonucleotides may also comprise single-or double-stranded ribonucleotide, RNA:DNA hybrids and double-stranded DNAs.

Methods of Use

The present invention also relates to assays and methods, both quantitative and qualitative, for detecting, diagnosing, monitoring, staging and prognosticating cancers by comparing levels of MSG in a human patient with those of MSG in a normal human control. For purposes of the present invention, what is meant by "MSG levels" is, among other things, native protein expressed by a polynucleotide sequence comprising SEQ ID NO: 1, 2, 3, 4, 5, 6, 7, 8, 9, 10, 11, 12, 13, 14, 15, 16, 17, 18, 19 or 20. By "MSG" it is also meant herein polynucleotides which, due to degeneracy in genetic coding, comprise variations in nucleotide sequence as compared to SEQ ID NO: 1, 2, 3, 4, 5, 6, 7, 8, 9, 10, 11, 12, 13, 14, 15, 16, 17, 18, 19 or 20, but which still encode the same protein. The native protein being detected may be whole, a breakdown product, a complex of molecules or chemically modified. In the alternative, what is meant by "MSG" as used herein, means the native mRNA encoded by the gene comprising the polynucleotide sequence of SEQ ID NO: 1, 2, 3, 4, 5, 6, 7, 8, 9, 10, 11, 12, 13, 14, 15, 16, 17, 18, 19 or 20, or a polynucleotide which is capable of hybridizing under stringent conditions to the antisense sequence of SEQ ID NO: 1, 2, 3, 4, 5, 6, 7, 8, 9, 10, 11, 12, 13, 14, 15, 16, 17, 18, 19 or 20. Such levels are preferably determined in at least one of cells, tissues and/or bodily fluids, including determination of normal and abnormal levels. Thus, for instance, a diagnostic assay in accordance with the invention for diagnosing overexpression of MSG protein compared to normal control bodily fluids, cells, or tissue samples may be used to diagnose the presence of mammary gland cancer.

All the methods of the present invention may optionally include determining the levels of other cancer markers as well as MSG. Other cancer markers, in addition to MSG, useful in the present invention will depend on the cancer being tested and are known to those of skill in the art.

Diagnostic Assays

The present invention provides methods for diagnosing the presence of cancer, and in particular mammary gland cancer, by analyzing for changes in levels of MSG in cells, tissues or bodily fluids compared with levels of MSG in cells, tissues or bodily fluids of preferably the same type from a normal human control, wherein an increase in levels of MSG in the patient versus the normal human control is associated with the presence of mammary gland cancer.

Without limiting the instant invention, typically, for a quantitative diagnostic assay a positive result indicating the patient being tested has cancer is one in which cells, tissues or bodily fluid levels of the cancer marker, such as MSG, are at least two times higher, and most preferably are at least five times higher, than in preferably the same cells, tissues or bodily fluid of a normal human control.

The present invention also provides a method of diagnosing metastatic mammary gland cancer in a patient having mammary gland cancer which has not yet metastasized for the onset of metastasis. In the method of the present invention, a human cancer patient suspected of having mammary gland cancer which may have metastasized (but which was not previously known to have metastasized) is identified. This is accomplished by a variety of means known to those of skill in the art.

In the present invention, determining the presence of MSG levels in cells, tissues or bodily fluid, is particularly useful for discriminating between mammary gland cancer which has not metastasized and mammary gland cancer which has metastasized. Existing techniques have difficulty discriminating between mammary gland cancer which has metastasized and mammary gland cancer which has not metastasized and proper treatment selection is often dependent upon such knowledge.

In the present invention, the cancer marker levels are measured in such cells, tissues or bodily fluid is MSG, and are then compared with levels of MSG in preferably the same cells, tissue or bodily fluid type of a normal human control. That is, if the cancer marker being observed is MSG in serum, this level is preferably compared with the level of MSG in serum of a normal human control. An increase in the MSG in the patient versus the normal human control is associated with mammary gland cancer which has metastasized.

Without limiting the instant invention, typically, for a quantitative diagnostic assay a positive result indicating the cancer in the patient being tested or monitored has metastasized is one in which cells, tissues or bodily fluid levels of the cancer marker, such as MSG, are at least two times higher, and most preferably are at least five times higher, than in preferably the same cells, tissues or bodily fluid of a normal patient.

Normal human control as used herein includes a human patient without cancer and/or non cancerous samples from the patient. In the methods for diagnosing or monitoring for metastasis, normal human control may preferably also include samples from a human patient that is determined by reliable methods to have mammary gland cancer which has not metastasized.

Staging

The invention also provides a method of staging mammary gland cancer in a human patient. The method comprises identifying a human patient having such cancer and analyzing cells, tissues or bodily fluid from such human patient for MSG. The MSG levels determined in the patient are then compared with levels of MSG in preferably the same cells, tissues or bodily fluid type of a normal human control, wherein an increase in MSG levels in the human patient versus the normal human control is associated with a cancer which is progressing and a decrease in the levels of MSG (but still increased over true normal levels) is associated with a cancer which is regressing or in remission.

Monitoring

Further provided is a method of monitoring mammary gland cancer in a human patient having such cancer for the onset of metastasis. The method comprises identifying a human patient having such cancer that is not known to have metastasized; periodically analyzing cells, tissues or bodily fluid from such human patient for MSG; and comparing the MSG levels determined in the human patient with levels of MSG in preferably the same cells, tissues or bodily fluid type of a normal human control, wherein an increase in MSG levels in the human patient versus the normal human control is associated with a cancer which has metastasized. In this method, normal human control samples may also include prior patient samples.

Further provided by this invention is a method of monitoring the change in stage of mammary gland cancer in a human patient having such cancer. The method comprises identifying a human patient having such cancer; periodically analyzing cells, tissues or bodily fluid from such human patient for MSG; and comparing the MSG levels determined in the human patient with levels of MSG in preferably the same cells, tissues or bodily fluid type of a normal human control, wherein an increase in MSG levels in the human patient versus the normal human control is associated with a cancer which is progressing in stage and a decrease in the levels of MSG is associated with a cancer which is regressing in stage or in remission. In this method, normal human control samples may also include prior patient samples.

Monitoring a patient for onset of metastasis is periodic and preferably done on a quarterly basis. However, this may be done more or less frequently depending on the cancer, the particular patient, and the stage of the cancer.

Prognostic Testing and Clinical Trial Monitoring

The methods described herein can further be utilized as prognostic assays to identify subjects having or at risk of developing a disease or disorder associated with increased levels of MSG. The present invention provides a method in which a test sample is obtained from a human patient and MSG is detected. The presence of higher MSG levels as compared to normal human controls is diagnostic for the human patient being at risk for developing cancer, particularly mammary gland cancer.

The effectiveness of therapeutic agents to decrease expression or activity of the MSGs of the invention can also be monitored by analyzing levels of expression of the MSGs in a human patient in clinical trials or in in vitro screening assays such as in human cells. In this way, the gene expression pattern can serve as a marker, indicative of the physiological response of the human patient, or cells as the case may be, to the agent being tested.

Detection of Genetic Lesions or Mutations

The methods of the present invention can also be used to detect genetic lesions or mutations in MSG, thereby determining if a human with the genetic lesion is at risk for mammary gland cancer or has mammary gland cancer. Genetic lesions can be detected, for example, by ascertaining the existence of a deletion and/or addition and/or substitution of one or more nucleotides from the MSGs of this invention, a chromosomal rearrangement of MSG, aberrant modification of MSG (such as of the methylation pattern of the genomic DNA), the presence of a non-wild type splicing pattern of a mRNA transcript of MSG, allelic loss of MSG, and/or inappropriate post-translational modification of MSG protein. Methods to detect such lesions in the MSGs of this invention are known to those of skill in the art.

Assay Techniques

Assay techniques that can be used to determine levels of gene expression (including protein levels), such as MSG of the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Western Blot analyses, ELISA assays and proteomic approaches: two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to MSG, preferably a monoclonal antibody. In addition a reporter antibody generally is prepared which binds specifically to MSG. The reporter antibody is attached to a detectable reagent such as radioactive, fluorescent or enzymatic reagent, for example horseradish peroxidase enzyme or alkaline phosphatase.

To carry out the ELISA, antibody specific to MSG is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time MSG binds to the specific antibody attached to the polystyrene dish. Unbound sample is washed out with buffer. A reporter antibody specifically directed to MSG and linked to a detectable reagent such as horseradish peroxidase is placed in the dish resulting in binding of the reporter antibody to any monoclonal antibody bound to MSG. Unattached reporter antibody is then washed out. Reagents for peroxidase activity, including a calorimetric substrate are then added to the dish. Immobilized peroxidase, linked to MSG antibodies, produces a colored reaction product. The amount of color developed in a given time period is proportional to the amount of MSG protein present in the sample. Quantitative results typically are obtained by reference to a standard curve.

A competition assay can also be employed wherein antibodies specific to MSG are attached to a solid support and labeled MSG and a sample derived from the host are passed over the solid support. The amount of label detected which is attached to the solid support can be correlated to a quantity of MSG in the sample.

Using all or a portion of a nucleic acid sequence of a MSG of the present invention as a hybridization probe, nucleic acid methods can also be used to detect MSG mRNA as a marker for mammary gland cancer. Polymerase chain reaction (PCR) and other nucleic acid methods, such as ligase chain reaction (LCR) and nucleic acid sequence based amplification (NASBA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e. gridding) can be used to both detect the expression of and quantitate the level of expression of that gene. In this approach, a cDNA encoding the MSG gene is fixed to a substrate. The substrate may be of any suitable type including but not limited to glass, nitrocellulose, nylon or plastic. At least a portion of the DNA encoding the MSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood.

In Vivo Targeting of MSG/Mammary Gland Cancer Therapy

Identification of these MSGs is also useful in the rational design of new therapeutics for imaging and treating cancers, and in particular mammary gland cancer. For example, in one embodiment, antibodies which specifically bind to a MSG can be raised and used in vivo in patients suspected of suffering from mammary gland cancer. Antibodies which specifically bind MSG can be injected into a patient suspected of having mammary gland cancer for diagnostic and/or therapeutic purposes. Thus, another aspect of the present invention provides for a method for preventing the onset and treatment of mammary gland cancer in a human patient in need of such treatment by administering to the patient an effective amount of antibody. By "effective amount" it is meant the amount or concentration of antibody needed to bind to the target antigens expressed on the tumor to cause tumor shrinkage for surgical removal, or disappearance of the tumor. The binding of the antibody to the overexpressed MSG is believed to cause the death of the cancer cell expressing such MSG. The preparation and use of antibodies for in vivo diagnosis and treatment is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against MSG can be used in a similar manner. Labeled antibodies which specifically bind MSG can be injected into patients suspected of having mammary gland cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Presence of the label, as compared to imaging of normal tissue, permits determination of the spread of the cancer. The amount of label within an organ or tissue also allows determination of the presence or absence of cancer in that organ or tissue.

Antibodies which can be used in in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

Vaccines

Another aspect of the invention relates to compositions and methods for inducing an immunological response in a mammal In one embodiment, a mammal is inoculated with a MSG polypeptide, or a fragment or variant thereof, in an amount adequate to produce an antibody and/or T cell immune response against MSG polypeptide. In another embodiment, a vector directing expression of MSG polynucleotide in vivo is used to induce such an immunological response and to produce antibody. The immune response against the MSG polypeptide is expected to protect the mammal from diseases, in particular mammary gland cancer.

Thus, the present invention also relates to an immunological/vaccine formulation (composition) which, when introduced into a mammal, induces an immunological response in that mammal to MSG polypeptide wherein the composition comprises a MSG polypeptide, fragment or variant thereof or a vector expressing a MSG gene or fragment thereof. The vaccine formulation may further comprise a suitable carrier. Since MSG polypeptide may be broken down in the stomach, the vaccine formulation is preferably administered parenterally via subcutaneous, intramuscular, intravenous, or intradermal injection. Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, as sealed ampules and vials, and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The MSG polypeptides of the present invention can also be employed in screening processes for compounds which activate (agonists) or inhibit activation of (antagonists, or otherwise called inhibitors) the MSG polypeptides of the present invention. Thus, polypeptides of the invention can be used to identify agonists or antagonists from, for example, cells, cell-free preparations, chemical libraries, and natural product mixtures. These agonists or antagonists may be natural or modified substrates, ligands, receptors, enzymes, etc., as the case may be, of the polypeptides of the present invention; or may be structural or functional mimetics of the polypeptide of the present invention. See Coligan et al., *Current Protocols in Immunology* 1(2):Chapter 5 (1991).

MSG polypeptides are responsible for various biological functions, including pathologies such as mammary gland cancer. Accordingly, it is desirous to identify compounds which stimulate MSG polypeptides on the one hand (agonists) and which can inhibit the function of MSG polypeptides (antagonists) on the other hand. Agonists and antagonists can be employed for therapeutic and prophylactic purposes for conditions such as mammary gland cancer.

In general, such screening procedures involve using appropriate cells which express the MSG polypeptide or respond to MSG polypeptide of the present invention. Such cells include those from mammals, yeast, Drosophila and *E. coli*. Cells which express the MSG polypeptide (or cell membranes containing the expressed polypeptide) or respond to MSG polypeptides are then contacted with a candidate compound to observe binding, or stimulation or inhibition of a functional response. The MSG activity of the cells which were contacted with the candidate compounds is compared with the MSG activity in the same type of cells which were not contacted with the candidate compounds.

The assays may simply test binding of a candidate compound wherein adherence to the cells bearing the MSG polypeptide is detected by means of a label directly or indirectly associated with the candidate compound or in an assay involving competition with a labeled competitor. Further, these assays can test whether the candidate compound results in a signal generated by activation of the MSG polypeptide using detection systems appropriate to the cells bearing the MSG polypeptide. Inhibitors of activation are generally assayed in the presence of a known agonist and the effect of the candidate compound upon activation by the agonist is observed.

Alternatively, the assays may comprise the steps of mixing a candidate compound with a solution containing a MSG polypeptide to form a mixture, measuring MSG activity in the mixture, and comparing the MSG activity of the mixture to a standard.

The MSG polynucleotide, polypeptides and antibodies immunospecific for the polypeptides can also be used to configure assays for detecting the effect of added compounds on the production of MSG mRNA and polypeptides in cells. For example, an ELISA for measuring secreted or cell associated levels of MSG polypeptide using monoclonal and polyclonal antibodies can be constructed by standard methods known in the art. The ELISA can then be used to discover agents which may inhibit or enhance the production of MSG from suitably manipulated cells or tissues. Standard methods for conducting these screening assays are well understood in the art.

The MSG polypeptides can also be used to identify membrane bound or soluble receptors, if any, through standard receptor binding techniques known in the art. These include, but are not limited to, ligand binding and crosslinking assays in which the MSG is labeled with a radioactive isotope (e.g. $^{125}$I), chemically modified (e.g. biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of MSG which compete with the binding of MSG to receptors. Standard methods for conducting these screening assays are well understood in the art.

Examples of potential MSG polypeptide antagonists include, but are not limited to: antibodies; oligonucleotides or proteins which are closely related to the MSGs; ligands, substrates, receptors, and enzymes of the MSG polypeptides; fragment of these ligands, substrates, receptors and enzymes; and small molecules which bind to the polypeptide of the present invention so that the activity of the polypeptide is prevented.

Thus, the present invention also relates to screening kits for identifying agonists, antagonists, ligands, receptors, substrates, enzymes, etc. for MSG polypeptides; or compounds which decrease or enhance the production of MSG polypeptides. Such kits preferably comprise a MSG polypeptide; a recombinant cell expressing a MSG polypeptide or a cell membrane expressing a MSG polypeptide; and an antibody to a MSG polypeptide.

Prophylactic and Therapeutic Methods

This invention also relates to methods of treating abnormal conditions such as, mammary gland cancer, related to both an excess of and insufficient amounts of MSG polypeptide activity.

If the activity of MSG polypeptide is in excess, several approaches are available. One approach comprises administering to a subject an inhibitor compound (antagonist) as hereinabove described along with a pharmaceutically acceptable carrier in an amount effective to inhibit the function of the MSG polypeptide, such as, for example, by blocking the binding of ligands, substrates, enzymes, receptors, etc., or by inhibiting a second signal, and thereby alleviating the abnormal condition. In another approach, soluble forms of MSG polypeptides still capable of binding the ligand, substrate, enzymes, receptors, etc. in competition with endogenous MSG polypeptide can be administered. Typical embodiments of such competitors comprise fragments of the MSG polypeptide.

In still another approach, expression of the gene encoding endogenous MSG polypeptide can be inhibited using expression blocking techniques. Known blocking techniques involve the use of antisense sequences, either internally generated or separately administered. See, for example, O'Connor, J Neurochem (1991) 56:560 in Oligodeoxynucleotides as Antisense Inhibitors of Gene Expression, CRC Press, Boca Raton, Fla. (1988). Alternatively, oligonucleotides which form triple helices with the gene can be supplied. See, for example, Lee et al., Nucleic Acids Res (1979) 6:3073; Cooney et al., Science (1988) 241:456; Dervan et al., Science (1991) 251:1360. These oligomers can be administered per se or the relevant oligomers can be expressed in vivo.

Several approaches are also available for treating abnormal conditions related to an under-expression of MSG and its activity. One approach comprises administering to a subject a therapeutically effective amount of a compound which activates MSG polypeptide, i.e., an agonist as described above, in combination with a pharmaceutically acceptable carrier, to thereby alleviate the abnormal condition. Alternatively, gene therapy can be employed to effect the endogenous production of MSG by the relevant cells in the subject. For example, a polynucleotide of the invention can be engineered for expression in a viral vector such as a replication defective retroviral vector. The retroviral expression construct can then be isolated and introduced into a packaging cell transduced with a retroviral plasmid vector containing RNA encoding a polypeptide of the present invention such that the packaging cell now produces infectious viral particles containing the gene of interest. These producer cells can be administered to a subject for engineering cells in vivo and expression of the polypeptide in vivo. For an overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of MSG polypeptides in combination with a suitable pharmaceutical carrier.

Formulation and Administration

Peptides, such as a soluble form of MSG polypeptide, and agonist and antagonist peptides or small molecules, can be formulated in various combinations with suitable pharmaceutical carriers. These formulations comprise a therapeutically effective amount of the peptide or small molecule, and a pharmaceutically acceptable carrier or excipient. Such carriers include, but are not limited to, saline, buffered saline, dextrose, water, glycerol, ethanol, and combinations thereof. The formulation is selected in accordance with the mode of administration, and is well within the skill of the art. The invention further relates to pharmaceutical packs and kits comprising one or more containers filled with one or more of the ingredients of the aforementioned compositions of the invention.

The compositions of present invention can be employed alone or in conjunction with other compounds, such as other therapeutic compounds.

Preferred forms of systemic administration of these pharmaceutical compositions include injection, typically by intravenous injection. Other injection routes, such as subcutaneous, intramuscular, or intraperitoneal, can also be used. Alternative means for systemic administration include transmucosal and transdermal administration using penetrants such as bile salts or fusidic acids or other detergents. In addition, if properly formulated in enteric or encapsulated formulations, oral administration may also be possible. These compositions can also be administered topically in the form of salves, pastes, gels and the like.

The dosage range required depends on the composition, the route of administration, the nature of the formulation, the nature of the subject's condition, and the judgment of the attending practitioner. Suitable dosages, however, are generally in the range of 0.1–100 µg of peptide or small molecule per kg of subject. Wide variations in the needed dosage, however, are to be expected in view of the variety of compounds available and the differing efficiencies of various routes of administration. For example, oral administration is expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a MSG polynucleotide of the present invention, such as a DNA or RNA, to encode a polypeptide ex vivo, and for example, by the use of a retroviral plasmid vector to encode a polypeptide in vivo. The cells are then introduced into the subject.

EXAMPLES

The present invention is further described by the following examples. The examples are provided solely to illustrate the invention by reference to specific embodiments. These exemplifications, while illustrating certain aspects of the invention, do not portray the limitations or circumscribe the scope of the disclosed invention.

Examples are carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 1

Suppression Subtractive Hybridization (Clontech PCR-SELECT)

Clontech PCR-SELECT is a PCR based subtractive hybridization method designed to selectively enrich for cDNAs corresponding to mRNAs differentially expressed between two mRNA populations (Diatchenko et al. *Proc. Natl. Acad. Sci. USA*, Vol. 93, pp. 6025–6030, 1996).

In this method, cDNA is prepared from the two mRNA populations which are to be compared (Tester: cDNA population in which the differentially expressed messages are sought and Driver: cDNA population in which the differentially expressed transcripts are absent or low). The tester sample is separated in two parts and different PCR adapters are ligated to the 5' ends. Each tester is separately annealed to excess driver (first annealing) and then pooled and again annealed (second annealing) to excess driver. During the first annealing, sequences common to both populations anneal. Additionally, the concentration of high and low abundance messages are normalized since annealing is faster for abundant molecules due to the second order kinetics of hybridization. During the second annealing, cDNAs unique or overabundant to the tester can anneal together. Such molecules have different adapters at their ends. The addition of additional driver during the second annealing enhances the enrichment of the desired differentially expressed sequences. During subsequent PCR, molecules that have different adapters at each end amplify exponentially. Molecules which have identical adapters, or adapters at only one end, or no adapters (driver sequences) either do not amplify or undergo linear amplification. The end result is enrichment for cDNAs corresponding to differentially expressed messages (unique to the tester or upregulated in the tester).

This technique was used to identify transcripts unique to mammary gland tissues or messages overexpressed in mammary gland cancer. Pairs of matched samples isolated from the same patient, a cancer sample, and the "normal" adjacent tissue from the same tissue type were utilized. The mRNA from the cancer tissue is used as the "tester", and the non-cancer mRNA as a "driver". The non-cancer "driver" is from the same individual and tissue as the cancer sample (Matched). Alternatively the "driver" can be from a different individual but the same tissue as the tumor sample (unmatched). In some cases, mixtures of mRNAs derived from non-cancer tissue types different from the cancer tissue type were used as the "driver". This approach allows the identification of transcripts whose expression is specific or upregulated in the cancer tissue type analyzed.

Several subtracted libraries were generated for mammary gland. The product of the subtraction experiments was used to generate cDNA libraries. These cDNA libraries contain Expressed Sequence Tags (ESTs) from genes that are mammary gland cancer specific, or upregulated in mammary gland. Selected clones from each cDNA PCR Select library were sequenced and are depicted as SEQ ID NO: 1, 2, 3, 4, 5, 6, 7, 8, 9, 10, 11, 12, 13, 14, 15, 16, 17, 18, 19 or 20.

Example 2

Relative Quantitation of Gene Expression

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) is used as this endogenous control. To calculate relative quantitation between all the samples studied,the target RNA levels for one sample are used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene was examined for every example in normal and cancer tissue. Total RNA was extracted from normal tissues, cancer tissues, and from cancers and the corresponding matched adjacent tissues. Subsequently, first strand cDNA was prepared with reverse transcriptase and the polymerase chain reaction was done using primers and Taqman probe specific to each target gene. The results were analyzed using the ABI PRISM 7700 Sequence Detector. The absolute numbers are relative levels of expression of the target gene in a particular tissue compared to the calibrator tissue.

Leads evaluated using real-time quantitative PCR are named "mam" followed by a number (for example: mam028).

For comparison, similar mRNA expression analysis was performed for genes coding for the diagnostic markers PSA (Prostate Specific Antigen) and PLA2 (Phospholipase A2). PSA is the only cancer screening marker available in clinical laboratories. When the panel of normal pooled tissues was analyzed, PSA was expressed at very high levels in prostate, with a very low expression in breast and testis. After more than 55 matching samples from 14 different tissues were analyzed, the data corroborated the tissue specificity seen with normal tissue samples. PSA expression in cancer and normal adjacent tissue for 12 matching samples of prostate tissue was also compare. The relative levels of PSA were higher in 10 cancer samples (83%). Clinical data recently obtained support the utilization of PLA2 as a staging marker for late stages of prostate cancer. The mRNA expression data from these experiments showed overexpression of the mRNA in 8 out of the 12 prostate matching samples analyzed (66%). The tissue specificity for PLA2 was not as good as the one described for PSA. In addition to prostate, small intestine, liver, and pancreas also showed high levels of mRNA expression for PLA2.

Example 3

Semi-quantitative Polymerase Chain Reaction (SQ-PCR)

SQ-PCR is a method that utilizes end point PCR on serial dilutions of cDNA samples in order to determine relative expression patterns of genes of interest in multiple samples. Using random hexamer primed Reverse Transcription (RT) cDNA panels are created from total RNA samples. Gene specific primers are then used to amplify fragments using Polymerase Chain Reaction (PCR) technology from four 10× serial cDNA dilutions in duplicate. Relative expression levels of 0, 1, 10, 100 and 1000 are used to evaluate gene expression. A positive reaction in the most dilute sample indicates the highest relative expression value. This is determined by analysis of the sample reactions on a 2–4% agarose gel. The tissue samples used include 12 normal, 12 cancer and 6 pairs of tissue specific cancer and matching samples. Leads evaluated through this method are named sqmam followed by a number (for example: sqmam022)

| SEQ ID NO: | CLONE ID NO: | LEAD ID NO: |
|---|---|---|
| 1 | Mamc00000385 | mam021 |
| 4 | Mam600369434F1 | mam019 |
| 11 | Mam600372192F1 | sqmam022 |
| 15 | Mam600370727F1 | sqmam023 |
| 17 | Mam600356265F1 | mam018 |
| 18 | Mam600370568F1 | mam028 |

```
SEQ ID NO:1; Clone ID: Mamc00000385 (Mam021)
Real-Time quantitative PCR was done using
the following primers:
Mam021forward:    (SEQ ID NO:21)
5' CCATCGTCTTCCTTTATCCAACT 3'
Mam021 reverse:   (SEQ ID NO:22)
5'TGGGTGATTTCAGAGAACTGCT 3'
Q-PCR probe    (SEQ ID NO:23)
5' TCAATTATAGGCAAAGGAACTCACAGAAGAAAAC 3'
```

Table 1 shows the absolute numbers which are relative levels of expression of mam021 in 36 normal samples from 25 different tissues. All the values are compared to normal testis (calibrator). These RNA samples are commercially available pools, originated by pooling samples of a particular tissue from different individuals; except for the blood samples that they are normal samples from a single individual.

TABLE 1

| Mam021 in Pooled Tissue Samples | |
|---|---|
| Tissue | Normal |
| Adrenal Gland | 0.00 |
| Bladder | 0.00 |
| Brain | 0.00 |
| Cervix | 0.54 |
| Colon | 0.20 |
| Endometrium | 0.00 |
| Esophagus | 0.03 |
| Heart | 0.00 |
| Kidney | 0.12 |
| Liver | 0.00 |
| Lung | 0.00 |
| Mammary gland | 0.00 |
| Muscle | 0.00 |
| Ovary | 0.00 |
| Pancreas | 0.00 |
| Prostate | 1.39 |
| Rectum | 0.00 |
| Small Intestine | 0.00 |
| Spleen | 0.00 |
| Stomach | 0.27 |
| Testis | 1.00 |
| Thymus | 0.38 |
| Trachea | 0.00 |
| Uterus | 0.00 |
| Blood B1 | 0.00 |
| Blood B10 | 0.00 |
| Blood B11 | 0.00 |
| Blood B12 | 0.13 |
| Blood B13 | 0.00 |
| Blood B14 | 0.00 |
| Blood B15 | 0.00 |
| Blood B4 | 0.00 |
| Blood B5 | 0.00 |
| Blood B6 | 0.00 |
| Blood B7 | 0.00 |
| Blood B8 | 0.00 |

0.00 = Negative

The relative levels of expression in Table 1 show that mam021 mRNA expression is detected in the pool of a few normal tissue analyzed.

The absolute numbers in Table 1 were obtained analyzing pools of samples of a particular tissue from different individuals, except for the blood samples. They can not be compared to the absolute numbers originated from RNA obtained from tissue samples of a single individual in Table 2.

Table 2 shows the absolute numbers which are relative levels of expression of mam021 in 78 pairs of matching samples. All the values are compared to normal testis (calibrator). A matching pair is formed by mRNA from the cancer sample for a particular tissue and mRNA from the normal adjacent sample for that same tissue from the same individual. In addition, 1 unmatched cancer sample (from ovary) and 1 unmatched normal sample (from ovary) were also tested.

TABLE 2

Mam021 in Individual Tissue Samples

| Sample ID | Tissue | Cancer | Normal Adjacent Tissue | Normal | TNM stage | Stage | Type of Adenocarcinoma |
|---|---|---|---|---|---|---|---|
| Mam497M | mammary gland 1 | 7.89 | 0.16 | | T1 N0 M0 | Stage I | Ductal |
| Mam173M | mammary gland 2 | 0.00 | 0.18 | | T1 N0 M0 | Stage I | Ductal |
| MamS621 | mammary gland 3 | 37.27 | 0.00 | | T1c N0 MX | Stage I | Ductal |
| MamS516 | mammary gland 4 | 1.43 | 0.00 | | T1c N0 MX | Stage I | Ductal |
| Mam726M | mammary gland 5 | 2.88 | 0.00 | | T1 N1-2 MX | Stage IIA | Ductal |
| MamS079 | mammary gland 6 | 0.13 | 0.12 | | T1c N1-2 MX | | Ductal |
| mam517 | mammary gland 7 | 0.64 | 0.98 | | T1c N1-2 MX | | Ductal |
| mam59X | mammary gland 8 | 1.64 | 204.36 | | T1c NX MX | | Ductal |
| Mam19DN | mammary gland 9 | 11.04 | 0.18 | | T2 N0 M0 | Stage IIA | Ductal |
| Mam522 | mammary gland 10 | 0.39 | 0.00 | | T2 N0 MX | Stage IIA | Ductal |
| MamS127 | mammary gland 11 | 0.07 | 0.00 | | T2 N0 MX | Stage IIA | Ductal |
| mamB011X | mammary gland 12 | 0.12 | 1.21 | | T2 N0 MX | Stage IIA | Ductal |
| mam51DN | mammary gland 13 | 1.58 | 0.00 | | T2 N1 M0 | | Ductal |
| Mam162X | mammary gland 14 | 0.14 | 0.00 | | T2 N1-2 MX | | Ductal |
| MamS123 | mammary gland 15 | 23.67 | 5.48 | | T2 N1-2 MX | | Ductal |
| MamS997 | mammary gland 16 | 0.00 | 0.00 | | T2 N1-2 MX | | Ductal |
| mam220 | mammary gland 17 | 1.85 | 0.57 | | T2 N1-2 MX | | Ductal |
| mam245M | mammary gland 18 | 83.29 | 13.59 | | T2 N1-2 MX | Stage IIB | Ductal |
| Mam543M | mammary gland 19 | 0.09 | 0.00 | | T2 NX MX | Stage IIB | Ductal |
| Mam976M | mammary gland 20 | 0.22 | 0.00 | | T2 NX MX | | Ductal |
| Mam76DN | mammary gland 21 | 1.94 | 0.00 | | T3 N1 M0 | | Ductal |
| mam699F | mammary gland 22 | 0.27 | 1.32 | | T3 NX MX | | Ductal |
| mam42DN | mammary gland 23 | 663.98 | 0.71 | | T3a N1 M0 | Stage IIIA | Ductal |
| mamS570 | mammary gland 24 | 0.47 | 5.64 | | T1c N1-2 MX | | Ductal + Lobular |
| MamS918 | mammary gland 25 | 0.00 | 0.00 | | T1c NX MX | | Ductal + Tubular |
| MamS854 | mammary gland 26 | 6.45 | 0.00 | | T1c N0 MX | Stage I | Lobular |
| MamS967 | mammary gland 27 | 0.00 | 0.00 | | T2 N0 MX | Stage IIA | Lobular |
| Mam986 | mammary gland 28 | 0.26 | 0.14 | | T2 N0 M0 | Stage IIB | Lobular |
| Mam355 | mammary gland 29 | 20.53 | 0.00 | | T2 N1-2 MX | Stage IIB | Lobular |
| MamS699 | mammary gland 30 | 1.04 | 0.00 | | T2 N1-2 MX | | Lobular |
| MamA06X | mammary gland 31 | 0.69 | 0.00 | | T3 N0 MX | Stage IIB | Lobular |
| Bld32XK | bladder 1 | 0.00 | 0.05 | | | | |
| Bld66X | bladder 2 | 1.55 | 0.14 | | | | |
| BldTR17 | bladder 3 | 0.00 | 0.00 | | | | |
| Bld46XK | bladder 4 | 0.39 | 0.15 | | | | |
| BldTR14 | bladder 5 | 0.24 | 0.11 | | | | |
| ClnB56 | colon 1 | 0.00 | 0.00 | | | | |
| ClnDC63 | colon 2 | 0.00 | 0.00 | | | | |
| CvxKS52 | cervix 1 | 0.00 | 0.00 | | | | |
| CvxNK24 | cervix 2 | 0.04 | 0.00 | | | | |
| CvxKS83 | cervix 3 | 0.00 | 0.32 | | | | |
| CvxNK23 | cervix 4 | 0.00 | 0.00 | | | | |
| Endo10479 | endometrium 1 | 0.13 | 0.27 | | | | |
| Endo12XA | endometrium 2 | 6.41 | 0.00 | | | | |
| Endo28XA | endometrium 3 | 0.04 | 0.00 | | | | |
| Endo3AX | endometrium 4 | 0.00 | 0.00 | | | | |
| Endo5XA | endometrium 5 | 0.00 | 0.00 | | | | |
| Endo65RA | endometrium 6 | 0.00 | 0.00 | | | | |
| Kid6XD | kidney 1 | 0.00 | 0.01 | | | | |
| Kid710K | kidney 2 | 0.00 | 0.06 | | | | |
| Liv175L | liver 1 | 0.05 | 0.38 | | | | |
| Liv187L | liver 2 | 0.00 | 0.00 | | | | |
| Liv15XA | liver 3 | 0.04 | 0.00 | | | | |
| Lng47XQ | lung 1 | 0.00 | 0.00 | | | | |
| LngAC88 | lung 2 | 0.00 | 0.00 | | | | |
| LngAC90 | lung 3 | 0.00 | 0.00 | | | | |
| LngSQ80 | lung 4 | 0.00 | 0.00 | | | | |
| Ovr103X | ovary 1 | 14.93 | 5.24 | | | | |
| OvrA084 | ovary 2 | 15.51 | 8.51 | | | | |
| OvrG010 | ovary 3 | 0.15 | 1.60 | | | | |
| OvrG021 | ovary 4 | 0.96 | 4.21 | | | | |
| Ovr1118 | ovary 5 | 0.00 | | | | | |
| Ovr32RA | ovary 6 | | | 0.00 | | | |
| Pan77X | pancreas 1 | 0.00 | 0.00 | | | | |
| Pan82XP | pancreas 2 | 0.00 | 0.00 | | | | |
| Pro109XB | prostate 1 | 0.00 | 0.00 | | | | |
| Pro125XB | prostate 2 | 0.28 | 0.15 | | | | |
| Skn248S | skin 1 | 0.00 | 0.00 | | | | |
| Skn287S | skin 2 | 0.01 | 0.00 | | | | |
| SmIntH89 | small intestine 1 | 0.00 | 0.02 | | | | |
| SmInt21XA | small intestine 2 | 2.69 | 0.04 | | | | |
| Sto115S | stomach 1 | 0.00 | 0.00 | | | | |

TABLE 2-continued

Mam021 in Individual Tissue Samples

| Sample ID | Tissue | Cancer | Normal Adjacent Tissue | Normal | TNM stage | Stage | Type of Adenocarcinoma |
|---|---|---|---|---|---|---|---|
| Sto15S | stomach 2 | 0.27 | 0.00 | | | | |
| StoMT54 | stomach 3 | 0.00 | 0.00 | | | | |
| Thr590D | thyroid 1 | 0.00 | 0.00 | | | | |
| Tst647T | Testis 1 | 0.03 | 0.00 | | | | |
| Utr141XO | uterus 1 | 0.00 | 0.00 | | | | |
| Utr23XU | uterus 2 | 0.00 | 0.00 | | | | |
| Utr85XU | uterus 3 | 0.00 | 0.20 | | | | |
| Utr135XO | uterus 4 | 0.06 | 0.00 | | | | |

0.00 = Negative

Table 2 represents 158 samples in 17 different tissues. Table 1 and Table 2 represent a combined total of 194 samples in 27 human tissue types.

Comparisons of the level of mRNA expression in breast cancer samples and the normal adjacent tissue from the same individuals are shown in Table 2. Mam021 is expressed at higher levels in 21 of 31 (68%) cancer samples (mammary gland 1, 3–5, 9–11, 13–15, 17–21, 23, 26, 28–31) compared to normal adjacent tissue. In particular, Mam021 shows overexpression in 5 out of 6 (83%) lobular adenocarcinomas (mammary gland 26, 28–31).

CHROMOSOME LOCALIZATION: Blast result against the human genome database, showed that the sequence for mam021 (SEQ ID NO: 1) has 95–100% identity with a sequence in chromosome 16.

```
SEQ ID NO:4; Clone ID: Mam600369434F1(mam019)
Real-Time quantitative PCR was done using the
following primers:
Mam019 forward:                     (SEQ ID NO:24)
5' GTGGCTCTTTCTTTTCCCTCAG 3'
Mam019 reverse:                     (SEQ ID NO:25)
5' CGCAGAGAGACAACCCAAGA 3'
Q-PCR probe                         (SEQ ID NO:26)
5' ACCTGCTGTTGCTCCTGGCTAGTCTTG 3'
```

Table 3 shows the absolute numbers which are relative levels of expression of mam019 in 36 normal samples from 25 different tissues. All the values are compared to normal uterus (calibrator). These RNA samples are commercially available pools, originated by pooling samples of a particular tissue from different individuals; except for the blood samples that they are normal samples from a single individual.

TABLE 3

Mam019 in Pooled Tissue Samples

| Tissue | Normal |
|---|---|
| Adrenal Gland | 0.11 |
| Bladder | 0.25 |
| Brain | 0.54 |
| Cervix | 0.27 |
| Colon | 0.27 |
| Endometrium | 0.63 |
| Esophagus | 0.03 |
| Heart | 0.81 |
| Kidney | 0.13 |
| Liver | 0.04 |
| Lung | 15.62 |
| Mammary gland | 6.92 |
| Muscle | 0.07 |
| Ovary | 0.51 |
| Pancreas | 0.00 |
| Prostate | 2.23 |
| Rectum | 0.13 |
| Small Intestine | 0.08 |
| Spleen | 2.94 |
| Stomach | 0.23 |
| Testis | 0.72 |
| Thymus | 0.43 |
| Trachea | 0.40 |
| Uterus | 1.00 |
| Blood B1 | 2.69 |
| Blood B10 | 5.43 |
| Blood B11 | 5.12 |
| Blood B12 | 7.94 |
| Blood B13 | 3.73 |
| Blood B14 | 11.59 |
| Blood B15 | 5.45 |
| Blood B4 | 5.78 |
| Blood B5 | 7.67 |
| Blood B6 | 1.59 |
| Blood B7 | 5.43 |
| Blood B8 | 5.88 |

0.00 = Negative

The relative levels of expression in Table 3 show that mam019 mRNA expression is detected in the pool of most of the normal tissue analyzed, being lung and mammary gland the highest expressers. Blood samples from single individuals showed expression levels that ranged from 1.59 to 11.59.

The absolute numbers in Table 3 were obtained analyzing pools of samples of a particular tissue from different individuals, except for the blood samples. They can not be compared to the absolute numbers originated from RNA obtained from tissue samples of a single individual in Table 4.

Table 4 shows the absolute numbers which are relative levels of expression of mam019 in 78 pairs of matching samples. All the values are compared to normal uterus (calibrator). A matching pair is formed by mRNA from the cancer sample for a particular tissue and mRNA from the normal adjacent sample for that same tissue from the same individual. In addition, 1 unmatched cancer sample (from ovary) and 1 unmatched normal sample (from ovary) were also tested.

TABLE 4

Mam0l9 in Individual Tissue Samples

| Sample ID | Tissue | Cancer | Normal Adjacent Tissue | Normal | TNM stage | Stage | Type of Adenocarcinoma |
|---|---|---|---|---|---|---|---|
| Mam497M | mammary gland 1 | 17.57 | 2.89 | | T1 N0 M0 | Stage I | Ductal |
| Mam173M | mammary gland 2 | 0.41 | 1.73 | | T1 N0 M0 | Stage I | Ductal |
| MamS516 | mammary gland 3 | 0.71 | 1.92 | | T1c N0 MX | Stage I | Ductal |
| MamS621 | mammary gland 4 | 6.32 | 1.14 | | T1c N0 MX | Stage I | Ductal |
| Mam726M | mammary gland 5 | 0.12 | 2.27 | | T1 N1-2 MX | Stage IIA | Ductal |
| MamS079 | mammary gland 6 | 3.71 | 2.34 | | T1c N1-2 MX | | Ductal |
| Mam517 | mammary gland 7 | 1.04 | 1.44 | | T1c N1-2 MX | | Ductal |
| Mam59X | mammary gland 8 | 2.11 | 5.05 | | T1c NX MX | | Ductal |
| Mam19DN | mammary gland 9 | 6.94 | 5.45 | | T2 N0 M0 | Stage IIA | Ductal |
| Mam522 | mammary gland 10 | 11.04 | 0.55 | | T2 N0 MX | Stage IIA | Ductal |
| MamS127 | mammary gland 11 | 0.00 | 0.04 | | T2 N0 MX | Stage IIA | Ductal |
| MamB011X | mammary gland 12 | 0.96 | 11.55 | | T2 N0 MX | Stage IIA | Ductal |
| Mam51DN | mammary gland 13 | 75.32 | 34.66 | | T2 N1 M0 | | Ductal |
| Mam162X | mammary gland 14 | 0.00 | 0.00 | | T2 N1-2 MX | | Ductal |
| MamS123 | mammary gland 15 | 0.00 | 0.00 | | T2 N1-2 MX | | Ductal |
| MamS997 | mammary gland 16 | 0.00 | 0.00 | | T2 N1-2 MX | | Ductal |
| Mam220 | mammary gland 17 | 6.28 | 37.27 | | T2 N1-2 MX | | Ductal |
| Mam245M | mammary gland 18 | 14.72 | 3.78 | | T2 N1-2 MX | Stage IIB | Ductal |
| Mam543M | mammary gland 19 | 0.32 | 0.05 | | T2 NX MX | Stage IIB | Ductal |
| Mam976M | mammary gland 20 | 0.00 | 0.00 | | T2 NX MX | | Ductal |
| Mam76DN | mammary gland 21 | 0.22 | 1.39 | | T3 N1 M0 | | Ductal |
| Mam699F | mammary gland 22 | 1.06 | 2.59 | | T3 NX MX | | Ductal |
| Mam42DN | mammary gland 23 | 6.02 | 10.63 | | T3a N1 M0 | Stage IIIA | Ductal |
| mamS570 | mammary gland 24 | 3.05 | 70.28 | | T1c N1-2 MX | | Ductal + Lobular |
| MamS918 | mammary gland 25 | 80.17 | 9.51 | | T1c NX MX | | Ductal + Tubular |
| MamS854 | mammary gland 26 | 0.00 | 0.03 | | T1c N0 MX | Stage I | Lobular |
| MamS967 | mammary gland 27 | 0.00 | 0.00 | | T2 N0 MX | Stage IIA | Lobular |
| Mam986 | mammary gland 28 | 4.68 | 7.09 | | T2 N0 M0 | Stage IIB | Lobular |
| Mam355 | mammary gland 29 | 24.34 | 0.06 | | T2 N1-2 MX | Stage IIB | Lobular |
| MamS699 | mammary gland 30 | 7.36 | 1.78 | | T2 N1-2 MX | | Lobular |
| MamA06X | mammary gland 31 | 76.90 | 1.34 | | T3 N0 MX | Stage IIB | Lobular |
| Bld32XK | bladder 1 | 0.72 | 0.24 | | | | |
| Bld66X | bladder 2 | 0.13 | 0.09 | | | | |
| BldTR17 | bladder 3 | 0.72 | 0.38 | | | | |
| Bld46XK | bladder 4 | 0.14 | 0.19 | | | | |
| BldTR14 | bladder 5 | 0.61 | 0.21 | | | | |
| ClnB56 | colon 1 | 0.84 | 1.13 | | | | |
| ClnDC63 | colon 2 | 0.36 | 1.50 | | | | |
| CvxKS52 | cervix 1 | 11.27 | 1.52 | | | | |
| CvxNK24 | cervix 2 | 0.83 | 0.64 | | | | |
| CvxKS83 | cervix 3 | 0.18 | 1.48 | | | | |
| CvxNK23 | cervix 4 | 0.08 | 0.28 | | | | |
| Endo10479 | endometrium 1 | 0.32 | 0.80 | | | | |
| Endo12XA | endometrium 2 | 0.30 | 1.61 | | | | |
| Endo5XA | endometrium 3 | 0.22 | 2.40 | | | | |
| Endo65RA | endometrium 4 | 0.00 | 0.00 | | | | |
| Endo28XA | endometrium 5 | 0.61 | 0.66 | | | | |
| Endo3AX | endometrium 6 | 0.43 | 0.00 | | | | |
| Kid6XD | kidney 1 | 0.15 | 0.27 | | | | |
| Kid710K | kidney 2 | 0.10 | 0.18 | | | | |
| Liv175L | liver 1 | 1.65 | 1.05 | | | | |
| Liv187L | liver 2 | 0.21 | 8.94 | | | | |
| Liv15XA | liver 3 | 0.13 | 0.06 | | | | |
| Lng47XQ | lung 1 | 0.20 | 11.20 | | | | |
| LngAC88 | lung 2 | 5.22 | 9.58 | | | | |
| LngAC90 | lung 3 | 0.90 | 1.03 | | | | |
| LngSQ80 | lung 4 | 2.76 | 1.61 | | | | |
| Ovr103X | ovary 1 | 0.36 | 0.08 | | | | |
| OvrA084 | ovary 2 | 0.39 | 0.11 | | | | |
| OvrG010 | ovary 3 | 0.32 | 0.03 | | | | |
| OvrG021 | ovary 4 | 0.05 | 0.21 | | | | |
| Ovr1118 | ovary 5 | 0.03 | | | | | |
| Ovr32RA | ovary 6 | | | 0.00 | | | |
| Pan77X | pancreas 1 | 0.61 | 0.47 | | | | |
| Pan82XP | pancreas 2 | 0.50 | 1.59 | | | | |
| Pro109XB | prostate 1 | 1.69 | 2.87 | | | | |
| Pro125XB | prostate 2 | 0.91 | 0.38 | | | | |
| Skn248S | skin 1 | 55.33 | 0.26 | | | | |
| Skn287S | skin 2 | 0.97 | 1.70 | | | | |
| SmIntH89 | small intestine 1 | 4.63 | 0.09 | | | | |
| SmInt21XA | small intestine 2 | 0.94 | 0.29 | | | | |
| Sto115S | stomach 1 | 1.78 | 0.62 | | | | |
| Sto15S | stomach 2 | 0.17 | 0.20 | | | | |

TABLE 4-continued

Mam019 in Individual Tissue Samples

| Sample ID | Tissue | Cancer | Normal Adjacent Tissue | Normal | TNM stage | Stage | Type of Adenocarcinoma |
|---|---|---|---|---|---|---|---|
| StoMT54 | stomach 3 | 0.25 | 0.29 | | | | |
| Thr590D | thyroid 1 | 0.70 | 0.45 | | | | |
| Tst647T | testis 1 | 0.20 | 0.00 | | | | |
| Utr141XO | uterus 1 | 1.06 | 0.47 | | | | |
| Utr23XU | uterus 2 | 1.19 | 0.39 | | | | |
| Utr85XU | uterus 3 | 0.00 | 0.26 | | | | |
| Utr135XO | uterus 4 | 0.90 | 0.38 | | | | |

0.00 = Negative

Table 4 represents 158 samples in 17 different tissues. Table 3 and Table 4 represent a combined total of 194 samples in 26 human tissue types.

Comparisons of the level of mRNA expression in breast cancer samples and the normal adjacent tissue from the same individuals are shown in Table 4. Mam019 is expressed at higher levels in 11 of 31 (35%) cancer samples (mammary gland 1, 4, 6, 10, 13, 18, 19, 25, 29–31) compared to normal adjacent tissue. If only the lobular adenocarcinomas samples are taking into account, 50% of the samples showed over-expression in cancer compared to normal adjacent tissue (mammary gland 29–31).

CHROMOSOME LOCALIZATION: Blast result against the human genome database, showed that the sequence listed below for mam019 (SEQ ID NO: 4) has 95–100% identity with a sequence in chromosome 10.

```
SEQ ID NO:17; Mam600356265F1 (mam018)
Real-Time quantitative PCR was done using the
following primers:
Mam018 forward:               (SEQ ID NO:27)
5' TCCATCTCCACGAGGTTGTG 3'
Mam018 reverse:               (SEQ ID NO:28)
5' GCCTTGCCTGTCTCACCAT 3'
Q-PCR probe                   (SEQ ID NO:29)
5' TGTCTAACTGATGGCTCTCATGCTGTAGTG 3'
```

Table 5 shows the absolute numbers which are relative levels of expression of mam018 in 36 normal samples from 25 different tissues. All the values are compared to normal muscle (calibrator). These RNA samples are commercially available pools, originated by pooling samples of a particular tissue from different individuals; except for the blood samples that they are normal samples from a single individual.

TABLE 5

Mam018 in Pooled Tissue Samples

| Tissue | Normal |
|---|---|
| Adrenal Gland | 0.00 |
| Bladder | 0.00 |
| Brain | 0.02 |
| Cervix | 0.00 |
| Colon | 0.00 |
| Endometrium | 0.00 |
| Esophagus | 0.15 |
| Heart | 0.00 |
| Kidney | 0.00 |
| Liver | 0.00 |
| Lung | 0.16 |
| Mammary gland | 0.78 |

TABLE 5-continued

Mam018 in Pooled Tissue Samples

| Tissue | Normal |
|---|---|
| Muscle | 1.00 |
| Ovary | 0.00 |
| Pancreas | 0.00 |
| Prostate | 0.00 |
| Rectum | 0.00 |
| Small Intestine | 0.00 |
| Spleen | 0.00 |
| Stomach | 0.00 |
| Testis | 0.00 |
| Thymus | 0.20 |
| Trachea | 0.14 |
| Uterus | 0.00 |
| Blood B1 | 0.00 |
| Blood B10 | 0.00 |
| Blood B11 | 0.03 |
| Blood B12 | 0.00 |
| Blood B13 | 0.01 |
| Blood B14 | 0.05 |
| Blood B15 | 0.06 |
| Blood B4 | 0.00 |
| Blood B5 | 0.00 |
| Blood B6 | 0.00 |
| Blood B7 | 0.03 |
| Blood B8 | 0.05 |

0.00 = Negative

The relative levels of expression in Table 5 show that mam018 mRNA expression is detected in the pool of a few normal tissue analyzed.

The absolute numbers in Table 5 were obtained analyzing pools of samples of a particular tissue from different individuals, except for the blood samples. They can not be compared to the absolute numbers originated from RNA obtained from tissue samples of a single individual in Table 6.

Table 6 shows the absolute numbers which are relative levels of expression of mam018 in 73 pairs of matching samples. All the values are compared to normal muscle (calibrator). A matching pair is formed by mRNA from the cancer sample for a particular tissue and mRNA from the normal adjacent sample for that same tissue from the same individual. In addition, 1 unmatched cancer sample (from ovary) and 1 unmatched normal sample (from ovary) were also tested.

TABLE 6

Mam018 in Individual Tissue Samples

| Sample ID | Tissue | Cancer | Normal Adjacent Tissue | Normal | TNM stage | Stage | Type of Adenocarcinoma |
|---|---|---|---|---|---|---|---|
| Mam497M | mammary gland 1 | 0.11 | 0.64 | | T1 N0 M0 | Stage I | Ductal |
| Mam173M | mammary gland 2 | 0.08 | 0.56 | | T1 N0 M0 | Stage I | Ductal |
| MamS516 | mammary gland 3 | 0.15 | 0.00 | | T1c N0 MX | Stage I | Ductal |
| MamS621 | mammary gland 4 | 0.05 | 0.00 | | T1c N0 MX | Stage I | Ductal |
| Mam726M | mammary gland 5 | 0.10 | 3.66 | | T1 N1-2 MX | Stage IIA | Ductal |
| MamS079 | mammary gland 6 | 0.49 | 0.14 | | T1c N1-2 MX | | Ductal |
| MamS517 | mammary gland 7 | 0.00 | 0.00 | | T1c N1-2 MX | | Ductal |
| Mam59X | mammary gland 8 | 57.68 | 1.14 | | T1c NX MX | | Ductal |
| Mam19DN | mammary gland 9 | 1.08 | 0.70 | | T2 N0 M0 | Stage IIA | Ductal |
| Mam522 | mammary gland 10 | 0.06 | 0.04 | | T2 N0 MX | Stage IIA | Ductal |
| MamS127 | mammary gland 11 | 0.10 | 0.29 | | T2 N0 MX | Stage IIA | Ductal |
| MamB011X | mammary gland 12 | 36.76 | 0.25 | | T2 N0 MX | Stage IIA | Ductal |
| Mam51DN | mammary gland 13 | 0.22 | 1.60 | | T2 N1 M0 | | Ductal |
| Mam162X | mammary gland 14 | 0.04 | 0.13 | | T2 N1-2 MX | | Ductal |
| MamS123 | mammary gland 15 | 0.28 | 0.00 | | T2 N1-2 MX | | Ductal |
| MamS997 | mammary gland 16 | 105.79 | 3.82 | | T2 N1-2 MX | | Ductal |
| Mam220 | mammary gland 17 | 0.22 | 0.00 | | T2 N1-2 MX | | Ductal |
| Mam245M | mammary gland 18 | 2.94 | 0.38 | | T2 N1-2 MX | Stage IIB | Ductal |
| Mam543M | mammary gland 19 | 0.00 | 0.01 | | T2 NX MX | Stage IIB | Ductal |
| Mam976M | mammary gland 20 | 0.00 | 0.16 | | T2 NX MX | | Ductal |
| Mam76DN | mammary gland 21 | 0.31 | 1.21 | | T3 N1 M0 | | Ductal |
| Mam699F | mammary gland 22 | 7.49 | 9.99 | | T3 NX MX | | Ductal |
| Mam42DN | mammary gland 23 | 0.03 | 0.24 | | T3a N1 M0 | Stage IIIA | Ductal |
| MamS570 | mammary gland 24 | 0.00 | 0.79 | | T1c N1-2 MX | | Ductal + Lobular |
| MamS918 | mammary gland 25 | 0.07 | 0.22 | | T1c NX MX | | Ductal + Tubular |
| MamS854 | mammary gland 26 | 0.53 | 0.00 | | T1c N0 MX | Stage I | Lobular |
| MamS967 | mammary gland 27 | 0.00 | 0.09 | | T2 N0 MX | Stage IIA | Lobular |
| Mam986 | mammary gland 28 | 0.00 | 0.01 | | T2 N0 M0 | Stage IIB | Lobular |
| Mam355 | mammary gland 29 | 0.04 | 0.04 | | T2 N1-2 MX | Stage IIB | Lobular |
| MamS699 | mammary gland 30 | 0.26 | 0.16 | | T2 N1-2 MX | | Lobular |
| MamA06X | mammary gland 31 | 0.07 | 0.05 | | T3 N0 MX | Stage IIB | Lobular |
| Bld32XK | bladder 1 | 0.00 | 0.00 | | | | |
| Bld66X | bladder 2 | 0.00 | 0.00 | | | | |
| BldTR17 | bladder 3 | 0.00 | 0.00 | | | | |
| Bld46XK | bladder 4 | 0.09 | 0.05 | | | | |
| BldTR14 | bladder 5 | 0.12 | 0.15 | | | | |
| ClnB56 | colon 1 | 0.00 | 0.00 | | | | |
| ClnDC63 | colon 2 | 0.00 | 0.00 | | | | |
| CvxKS52 | cervix 1 | 0.01 | 0.00 | | | | |
| CvxNK24 | cervix 2 | 0.01 | 0.00 | | | | |
| CvxKS83 | cervix 3 | 0.00 | 0.00 | | | | |
| CvxNK23 | cervix 4 | 0.07 | 0.00 | | | | |
| Endo10479 | endometrium 1 | 0.00 | 0.00 | | | | |
| Endo12XA | endometrium 2 | 0.00 | 0.06 | | | | |
| Endo5XA | endometrium 3 | 0.00 | 0.00 | | | | |
| Endo65RA | endometrium 4 | 0.00 | 0.00 | | | | |
| Endo28XA | endometrium 5 | 0.00 | 0.00 | | | | |
| Endo3AX | endometrium 6 | 0.00 | 0.00 | | | | |
| Kid6XD | kidney 1 | 0.01 | 0.00 | | | | |
| Kid710K | kidney 2 | 0.00 | 0.00 | | | | |
| Liv175L | liver 1 | 0.00 | 0.00 | | | | |
| Liv187L | liver 2 | 0.00 | 0.00 | | | | |
| Liv15XA | liver 3 | 0.00 | 0.00 | | | | |
| Lng47XQ | lung 1 | 0.01 | 0.00 | | | | |
| LngAC88 | lung 2 | 0.04 | 0.00 | | | | |
| LngAC90 | lung 3 | 0.00 | 0.00 | | | | |
| LngSQ80 | lung 4 | 0.01 | 0.00 | | | | |
| Ovr1118 | ovary 1 | 0.00 | | | | | |
| Ovr32RA | ovary 2 | | | 0.05 | | | |
| Pan77X | pancreas 1 | 0.00 | 0.00 | | | | |
| Pan82XP | pancreas 2 | 0.00 | 0.00 | | | | |
| Pro109XB | prostate 1 | 0.00 | 0.00 | | | | |
| Skn248S | skin 1 | 0.04 | 0.01 | | | | |
| Skn287S | skin 2 | 0.09 | 0.01 | | | | |
| SmIntH89 | small intestine 1 | 0.00 | 0.00 | | | | |
| SmInt21XA | small intestine 2 | 0.00 | 0.00 | | | | |
| Sto115S | stomach 1 | 0.01 | 0.00 | | | | |
| Sto15S | stomach 2 | 0.00 | 0.00 | | | | |
| StoMT54 | stomach 3 | 0.00 | 0.00 | | | | |
| Thr590D | thyroid 1 | 0.00 | 0.00 | | | | |
| Tst647T | testis 1 | 0.00 | 0.00 | | | | |
| Utr141XO | uterus 1 | 0.00 | 0.00 | | | | |
| Utr23XU | uterus 2 | 0.00 | 0.00 | | | | |

TABLE 6-continued

Mam018 in Individual Tissue Samples

| Sample ID | Tissue | Cancer | Normal Adjacent Tissue | Normal | TNM stage | Stage | Type of Adenocarcinoma |
|---|---|---|---|---|---|---|---|
| Utr85XU | uterus 3 | 0.00 | 0.00 | | | | |
| Utr135XO | uterus 4 | 0.00 | 0.00 | | | | |

0.00 = Negative

Table 6 represents 148 samples in 17 different tissues. Table 5 and Table 6 represent a combined total of 184 samples in 27 human tissue types.

Comparisons of the level of mRNA expression in breast cancer samples and the normal adjacent tissue from the same individuals are shown in Table 6. Mam018 is expressed at higher levels in 13 of 31 (42%) cancer samples (mammary gland 3, 4, 6, 8–10, 12, 15–18, and 30) compared to normal adjacent tissue.

CHROMOSOME LOCALIZATION: Blast result against the human genome database, showed that the sequence listed below for mam018 (SEQ ID NO: 17) has 95–100% identity with a sequence in chromosome 2.

```
SEQ ID NO:18; Mam600370568F1 (Mam028)
Real-Time quantitative PCR was done using the
following primers:
Mam028forward:                (SEQ ID NO:30)
5' AGAGGCTAAAAGCAACTTGTCC 3'
Mam028 reverse:               (SEQ ID NO:31)
5' GCAAAAACTCTCAGCAAACCTT 3'
Q-PCR probe                   (SEQ ID NO:32)
5' AGCCGTAAACTTTCTCATACACTTTGTCCA 3'
```

Table 7 shows the absolute numbers which are relative levels of expression of mam028 in 24 normal samples from 24 different tissues. All the values are compared to normal spleen (calibrator). These RNA samples are commercially available pools, originated by pooling samples of a particular tissue from different individuals.

TABLE 7 mam028 in Pooled Tissue Samples

| Tissue | Normal |
|---|---|
| Adrenal Gland | 0.00 |
| Bladder | 0.00 |
| Brain | 0.00 |
| Cervix | 0.01 |
| Colon | 0.00 |
| Endometrium | 0.00 |
| Esophagus | 0.00 |

TABLE 7-continued mam028 in Pooled Tissue Samples

| Tissue | Normal |
|---|---|
| Heart | 0.00 |
| Kidney | 0.00 |
| Liver | 0.00 |
| Lung | 0.14 |
| Mammary gland | 0.00 |
| Muscle | 0.00 |
| Ovary | 0.01 |
| Pancreas | 0.01 |
| Prostate | 0.01 |
| Rectum | 0.01 |
| Small Intestine | 0.00 |
| Spleen | 1.00 |
| Stomach | 0.00 |
| Testis | 0.00 |
| Thymus | 9.85 |
| Trachea | 0.01 |
| Uterus | 0.01 |

0.00 = Negative

The relative levels of expression in Table 7 show that mam028 mRNA expression is detected in the pool of a few of normal tissue analyzed.

The absolute numbers in Table 7 were obtained analyzing pools of samples of a particular tissue from different individuals, except for the blood samples. They can not be compared to the absolute numbers originated from RNA obtained from tissue samples of a single individual in Table 8.

Table 8 shows the absolute numbers which are relative levels of expression of mam028 in 49 pairs of matching samples. All the values are compared to normal spleen (calibrator). A matching pair is formed by mRNA from the cancer sample for a particular tissue and mRNA from the normal adjacent sample for that same tissue from the same individual. In addition, 1 unmatched cancer sample (from ovary) and 1 unmatched normal sample (from ovary) were also tested.

TABLE 8

Mam028 in Individual Tissue Samples

| Sample ID | Tissue | Cancer | Normal Adjacent Tissue | Normal | TNM stage | Stage | Type of Adenocarcinoma |
|---|---|---|---|---|---|---|---|
| Mam497M | mammary gland 1 | 0.00 | 0.00 | | T1 N0 M0 | Stage I | Ductal |
| Mam173M | mammary gland 2 | 0.01 | 0.07 | | T1 N0 M0 | Stage I | Ductal |
| MamS516 | mammary gland 3 | 0.03 | 0.00 | | T1c N0 MX | Stage I | Ductal |
| MamS621 | mammary gland 4 | 0.04 | 0.00 | | T1c N0 MX | Stage I | Ductal |

TABLE 8-continued

Mam028 in Individual Tissue Samples

| Sample ID | Tissue | Cancer | Normal Adjacent Tissue | Normal | TNM stage | Stage | Type of Adenocarcinoma |
|---|---|---|---|---|---|---|---|
| Mam726M | mammary gland 5 | 0.04 | 0.04 | | T1 N1-2 MX | Stage IIA | Ductal |
| MamS079 | mammary gland 6 | 0.14 | 0.00 | | T1c N1-2 MX | | Ductal |
| Mam19DN | mammary gland 7 | 0.00 | 0.00 | | T2 N0 M0 | Stage IIA | Ductal |
| Mam522 | mammary gland 8 | 0.01 | 0.00 | | T2 N0 MX | Stage IIA | Ductal |
| MamS127 | mammary gland 9 | 0.15 | 0.00 | | T2 N0 MX | Stage IIA | Ductal |
| Mam162X | mammary gland 10 | 0.02 | 0.01 | | T2 N1-2 MX | | Ductal |
| MamS123 | mammary gland 11 | 0.08 | 0.00 | | T2 N1-2 MX | | Ductal |
| MamS997 | mammary gland 12 | 0.10 | 0.01 | | T2 N1-2 MX | | Ductal |
| Mam543M | mammary gland 13 | 0.00 | 0.00 | | T2 NX MX | Stage IIB | Ductal |
| Mam976M | mammary gland 14 | 0.00 | 0.00 | | T2 NX MX | | Ductal |
| Mam76DN | mammary gland 15 | 0.63 | 0.07 | | T3 N1 M0 | | Ductal |
| MamS918 | mammary gland 16 | 0.02 | 0.02 | | T1c NX MX | | Ductal + Tubular |
| MamS854 | mammary gland 17 | 0.00 | 0.00 | | T1c N0 MX | Stage I | Lobular |
| MamS967 | mammary gland 18 | 0.34 | 0.04 | | T2 N0 MX | Stage IIA | Lobular |
| Mam986 | mammary gland 19 | 0.02 | 0.00 | | T2 N0 M0 | Stage IIB | Lobular |
| Mam355 | mammary gland 20 | 0.02 | 0.00 | | T2 N1-2 MX | Stage IIB | Lobular |
| MamA06X | mammary gland 21 | 0.01 | 0.00 | | T3 N0 MX | Stage IIB | Lobular |
| Bld46XK | bladder 1 | 0.00 | 0.00 | | | | |
| BldTR14 | bladder 2 | 0.24 | 0.04 | | | | |
| ClnB56 | colon 1 | 0.00 | 0.00 | | | | |
| ClnDC63 | colon 2 | 0.00 | 0.00 | | | | |
| CvxKS83 | cervix 1 | 0.03 | 0.04 | | | | |
| CvxNK23 | cervix 2 | 0.01 | 0.02 | | | | |
| Endo10479 | endometrium 1 | 0.06 | 0.07 | | | | |
| Endo12XA | endometrium 2 | 0.24 | 0.00 | | | | |
| Endo5XA | endometrium 3 | 0.00 | 0.00 | | | | |
| Endo65RA | endometrium 4 | 0.00 | 0.00 | | | | |
| Endo28XA | endometrium 5 | 0.00 | 0.01 | | | | |
| Endo3AX | endometrium 6 | 0.19 | 0.00 | | | | |
| Kid6XD | kidney 1 | 0.01 | 0.02 | | | | |
| Kid710K | kidney 2 | 0.00 | 0.00 | | | | |
| Liv15XA | liver 1 | 0.00 | 0.00 | | | | |
| Lng47XQ | lung 1 | 0.04 | 0.00 | | | | |
| LngAC88 | lung 2 | 0.84 | 0.09 | | | | |
| LngAC90 | lung 3 | 0.24 | 0.00 | | | | |
| LngSQ80 | lung 4 | 0.00 | 0.00 | | | | |
| Ovr1118 | ovary 1 | 0.01 | | | | | |
| Ovr32RA | ovary 2 | | | 0.06 | | | |
| Pan77X | pancreas 1 | 0.00 | 0.00 | | | | |
| Pan82XP | pancreas 2 | 0.01 | 0.00 | | | | |
| SmInt21XA | small intestine 1 | 0.01 | 0.01 | | | | |
| Sto115S | stomach 1 | 0.57 | 0.25 | | | | |
| Sto15S | stomach 2 | 0.01 | 0.07 | | | | |
| StoMT54 | stomach 3 | 0.00 | 0.00 | | | | |
| Thr590D | thyroid 1 | 0.14 | 0.00 | | | | |
| Tst647T | testis 1 | 0.01 | 0.00 | | | | |
| Utr135XO | uterus 1 | 0.02 | 0.00 | | | | |

0.00 = Negative

Table 8 represents 100 samples in 15 different tissues. Table 7 and Table 8 represent a combined total of 124 samples in 25 human tissue types.

Comparisons of the level of mRNA expression in breast cancer samples and the normal adjacent tissue from the same individuals are shown in Table 8. Mam019 is expressed at higher levels in 13 of 21 (62%) cancer samples (mammary gland 3, 4, 6, 8–12, 15, 18–21) compared to normal adjacent tissue. If only the lobular adenocarcinomas samples are taken into account, 80% of the samples showed overexpression in cancer compared to normal adjacent tissue (mammary gland 18–21).

CHROMOSOME LOCALIZATION: Blast result against the human genome database, showed that the sequence listed below for mam028 (SEQ ID NO: 18) has 95–100% identity with a sequence in chromosomes 6, and 15.

SEQ ID NO:11; Clone ID Mam600372192F1 (sqmam022)
Semi-quantitative PCR was done using the following primers:
sqmam022 forward: (SEQ ID NO:33)
5' GCAGCCTGAGGTGACTAATATCC 3'
sqmam022 reverse: (SEQ ID NO:34)
5' GCTTGTGTGAGAGTGTGCCTAAT 3'

Table 9 shows the absolute numbers which are relative levels of expression of sqmam022 in 12 normal samples from 12 different tissues. These RNA samples are from single individual or are commercially available pools, originated by pooling samples of a particular tissue from different individuals. Using Polymerase Chain Reaction (PCR) technology expression levels were analyzed from four 10 serial cDNA dilutions in duplicate. Relative expression levels of 0, 1, 10, 100 and 1000 are used to evaluate gene expression. A positive reaction in the most dilute sample indicates the highest relative expression value.

TABLE 9

Sqmam022 in Normal Tissue Samples

| TISSUE | NORMAL |
|---|---|
| Breast | 1 |
| Colon | 1 |
| Endometrium | 0 |
| Kidney | 0 |
| Liver | 0 |
| Lung | 0 |
| Ovary | 0 |
| Prostate | 1 |
| Small Intestine | 0 |
| Stomach | 0 |
| Testis | 10 |
| Uterus | 0 |

Relative levels of expression in Table 9 show that normal testes exhibit the highest expression of sqmam022, followed by breast, colon, and prostate.

Table 10 shows the absolute numbers which are relative levels of expression of sqmam022 in 12 cancer samples from 12 different tissues. Using Polymerase Chain Reaction (PCR) technology expression levels were analyzed from four 10 serial cDNA dilutions in duplicate. Relative expression levels of 0, 1, 10, 100 and 1000 are used to evaluate gene expression. A positive reaction in the most dilute sample indicates the highest relative expression value.

TABLE 10

Sqmam022 in Cancer Tissue Samples

| TISSUE | CANCER |
|---|---|
| bladder | 0 |
| breast | 1 |
| colon | 0 |
| kidney | 0 |
| liver | 1 |
| lung | 0 |
| ovary | 0 |
| pancreas | 0 |
| prostate | 0 |
| stomach | 0 |
| testes | 1 |
| uterus | 0 |

Relative levels of expression in Table 10 show that sqmam022 is expressed in breast, liver and testes carcinomas.

Table 11 shows the absolute numbers which are relative levels of expression of sqmam022 in 6 mammary gland cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10 serial cDNA dilutions in duplicate. Relative expression levels of 0, 1, 10, 100 and 1000 are used to evaluate gene expression. A positive reaction in the most dilute sample indicates the highest relative expression value.

TABLE 11

Sqmam022 in Mammary Gland Cancer Samples

| SAMPLE ID | TISSUE | CANCER | NORMAL ADJACENT TISSUE |
|---|---|---|---|
| S99522A/B | mammary gland 1 | 1 | 0 |
| 4005724A2/B3 | mammary gland 2 | 1 | 0 |
| 4005599A4/B2 | mammary gland 3 | 1 | 0 |
| 4005629A2/B2 | mammary gland 4 | 0 | 1 |
| S9822245A/B | mammary gland 5 | 0 | 0 |
| S9819997A/B | mammary gland 6 | 1 | 0 |

Relative levels of expression in Table 11 show that sqmam022 is expressed in four of the six mammary gland cancer samples with no expression in the matching normal adjacent tissue (NAT). This assay shows that sqmam022 is upregulated in 67% of the matching samples analyzed CHROMOSOME LOCALIZATION: Blast result against the human genome database, showed that the sequence listed below for sqmam022 (SEQ ID NO: 11) has 95–100% identity with a sequence in chromosome 11.

```
SEQ ID NO:15; Clone ID Mam600370727F1 (Sqmam023)
Semi-quantitative PCR was done using the
following primers:
sqmam023forward:                (SEQ ID NO:35)
5' TTCCAATTATTCTTTCTTTTGCTC 3'
sqmam023 reverse:               (SEQ ID NO:36)
5' AGTGCGTGGTGATGTCTAGTG 3'
```

Table 12 shows the absolute numbers which are relative levels of expression of sqmam023 in 12 normal samples from 12 different tissues. These RNA samples are from single individual or are commercially available pools, originated by pooling samples of a particular tissue from different individuals. Using Polymerase Chain Reaction (PCR) technology expression levels were analyzed from four 10 serial cDNA dilutions in duplicate. Relative expression levels of 0, 1, 10, 100 and 1000 are used to evaluate gene expression. A positive reaction in the most dilute sample indicates the highest relative expression value.

TABLE 12

Sqmam023 in Normal Tissue Samples

| TISSUES | NORMAL |
|---|---|
| Breast | 100 |
| Colon | 0 |
| Endometrium | 0 |
| Kidney | 1 |
| Liver | 0 |
| Lung | 0 |
| Ovary | 0 |
| Prostate | 1 |
| Small Intestine | 0 |
| Stomach | 0 |
| Testis | 0 |
| Uterus | 1 |

Relative levels of expression in Table 12 show that normal breast exhibit the highest expression of sqmam022, followed by kidney, prostate and uterus.

Table 13 shows the absolute numbers which are relative levels of expression of sqmam023 in 12 cancer samples from 12 different tissues. Using Polymerase Chain Reaction (PCR) technology expression levels were analyzed from four 10× serial cDNA dilutions in duplicate. Relative expression levels of 0, 1, 10, 100 and 1000 are used to evaluate gene expression. A positive reaction in the most dilute sample indicates the highest relative expression value.

TABLE 13

Sqmam023 in Cancer Tissue Samples

| TISSUES | CANCER |
|---|---|
| bladder | 0 |
| breast | 10 |
| colon | 0 |
| kidney | 1 |
| liver | 0 |
| lung | 0 |
| ovary | 0 |
| pancreas | 0 |
| prostate | 0 |
| stomach | 0 |
| testes | 0 |
| uterus | 0 |

Relative levels of expression in Table 13 show that sqmam023 is highly expressed in breast adenocarcinoma, followed by liver carcinoma.

Table 14 shows the absolute numbers which are relative levels of expression of sqmam023 in 6 mammary gland cancer matching samples. A matching pair is formed by mRNA from the cancer sample for a particular tissue and mRNA from the normal adjacent sample for that same tissue from the same individual. Using Polymerase Chain Reaction (PCR) technology expression levels were analyzed from four 10x serial cDNA dilutions in duplicate. Relative expression levels of 0, 1, 10, 100 and 1000 are used to evaluate gene expression. A positive reaction in the most dilute sample indicates the highest relative expression value.

TABLE 14

Sqmam023 in Mammary Gland Cancer Samples

| SAMPLE ID | TISSUE | CANCER | NORMAL ADJACENT TISSUE |
|---|---|---|---|
| S99522A/B | mammary gland 1 | 1 | 0 |
| 4005724A2/B3 | mammary gland 2 | 0 | 1 |
| 4005599A4/B2 | mammary gland 3 | 0 | 0 |
| 4005629A2/B2 | mammary gland 4 | 10 | 1 |
| S9822245A/B | mammary gland 5 | 0 | 10 |
| S9819997A/B | mammary gland 6 | 10 | 0 |

Relative levels of expression in Table 14 show that sqmam023 is overexpressed in three of the six mammary gland cancer samples with low or no expression in the matching normal adjacent tissue (NAT). This assay shows that sqmam023 is upregulated in 50% of the matching samples analyzed.

CHROMOSOME LOCALIZATION: Blast result against the human genome database, showed that the sequence listed below for sqmam023 (SEQ ID NO: 15) has 95–100% identity with a sequence in chromosome 10, and 85–90% identity with another sequence in the same chromosome.

What is claimed is:

1. An isolated polynucleotide comprising SEQ ID NO:1.
2. A vector comprising the polynucleotide of claim 1.
3. An isolated host cell expressing the vector of claim 2.
4. A method for producing a polypeptide recombinantly encoded by a nucleic acid sequence comprising SEQ ID:1 comprising culturing the host cell of claim 3 under conditions which promote expression of the nucleic acid sequence and isolating polypeptide expressed in the cells.
5. A method for producing a cell in culture expressing a polypeptide recombinantly encoded by a nucleic acid sequence comprising SEQ ID NO:1 comprising transforming or transfecting a cell with the vector of claim 2 so that the cell, under appropriate culture conditions, expresses said polypeptide.
6. An isolated fragment of SEQ ID NO:1 consisting of at least 15 contiguous bases.

* * * * *

SEQUENCE LISTING

<160> NUMBER OF SEQ ID NOS: 35

<210> SEQ ID NO 1
<211> LENGTH: 780
<212> TYPE: DNA
<213> ORGANISM: Homo sapiens

<400> SEQUENCE: 1

```
aattacttgt tctcttaaag taaggcctta caccctacta aaatgtgatc aaaattttat      60
tatgaataga tgaaaagctg tagctataaa ttatgagagt aagtttattt tatatttatc     120
caaatgtagt tcataatagc ataatagcaa cttcactaaa tcttagaata aaaaatgaat    180
aaaatgttaa ttttttggag gaaatggtta attttttcta caaaattgtg tgacagcttt    240
acagacctta ctcttcacaa ttgacttgaa cattaacatc acaaagaggg tcctgtttac    300
aaaagaatag tcaagaactt catgaatttt tgacagtgac tcttttctaa cccttaatc     360 caaatatatt taagtgtcca tcgtcttcct ttatccaact catttgttaa ctagttttct    420
tctgtgagtt cctttgccta taattgaagc agttctctga aatcacccaa actgatttta    480
tgaaagccca tgcttttgga aagatttgca cttcggcttt gcaatctatt tacattgact    540
gtacttgcat tgtattgcta gatgttgact atcagttagg acaatcaaaa agatattaga    600
taatgggcag ggataaatca gaagttactg tcaataacaa agttatgttt tatgggtatt    660
ttataggtga taaattcatt actgagcaat ttcatatcat gttttaattc tcctggttgt    720
aatatggtga ctctggagac tcaaatatta aatattggtg taaaggcaaa aaaaaaaaa     780
```

<210> SEQ ID NO 2
<211> LENGTH: 392

```
<212> TYPE: DNA
<213> ORGANISM: Homo sapiens

<400> SEQUENCE: 2
acaaaattat gcagagacta ctagatagcc attaaaatcc tctctcttct ccttccaaag      60
taatggaatt gaagctgacc acatggtcac ctagccacac gttcattggc atcctttcat    120
ttctaagttc cctccaatac aatgtgctgc ggggaagccg ctggtagctt aagatcctcc    180
tggcagctgt cacctgtatg taatggtgac ctagcttaat cagccaacaa tgccatagga    240
gatggtgcag cagatacctg aagggaatc ctaattcttt ctaatgtgca cagggattga    300
gctactcact accaggcacc ttaagactat ggaaagaaaa atacatgatt ttagtcattt    360
tggaggaggg aggcttggag gcttggaagc tt                                  392

<210> SEQ ID NO 3
<211> LENGTH: 280
<212> TYPE: DNA
<213> ORGANISM: Homo sapiens

<400> SEQUENCE: 3
actatcttta tgatgcttga atccaaactt gttcccacct ccaaaatgct tctgcagccc      60
ctatgttcct gaagcaaccc ctcttctctg gcctatagga cctccagcag gtgatggtgt    120
caggacccaa cctcaatgaa accagcattg tgtctggtgg ctatggggc tctggtgatg     180 gactcatccc cacaggtatg aatgttcaga acaggaatc ttgggtggag gaggggacag    240
gaatggtttg gggaagcata ggatatgtct aggaaagctt                          280

<210> SEQ ID NO 4
<211> LENGTH: 242
<212> TYPE: DNA
<213> ORGANISM: Homo sapiens

<400> SEQUENCE: 4
ctgagtttca gtcctggctc taccttctt ggcctgtggt tctaagcatg ttatttgcct      60
ctctcagctt caactgtgaa gagttcaatt aggtgatcac tttaactttt ctagctcgga    120
tactctgtgc cagctctgga accatgcttt ttggtgtctg tgtgtatata taggtcacct    180
gtatgtattt aggtctttga gaatctactg gactatcaaa aaaaaaaaaa acccacaaaa    240
ga                                                                   242

<210> SEQ ID NO 5
<211> LENGTH: 520
<212> TYPE: DNA
<213> ORGANISM: Homo sapiens

<400> SEQUENCE: 5
gccttaggtg atgcagcggt caagagttga aactcatgat tatggtatct tttccttcta     60
atctacaggg tgatgttgat ccttttccat ccggtgtcca ggcactctgt tgagagccaa    120
cgataagatc tgcagcttgt ggctcttttct tttccctcag gtgttgcacc tgctgttgct    180
cctggctagt cttgtcctca cctcagatcc tactgatgtt acctttcagg gatctagcaa    240
agattctctt ctgatcctat cttgggttgt ctctctgcga catttgctat gatgctactc    300
actcagctgt tgctagctag ctccacagcc acctctcacc tatttctggg cctcatctaa    360
acatataaaa accaaaattg gttcagaaaa ctaaatatca tggcctccct ctacttgctc    420
cagcaagtag atgtgaccct actcttagtt atctcaggat ggagtgctgc ccaagaagtg    480
```
atctatttca aaatcctgat tggaggagga agcaaagctt    520

<210> SEQ ID NO 6
<211> LENGTH: 218
<212> TYPE: DNA
<213> ORGANISM: Homo sapiens
<220> FEATURE:
<221> NAME/KEY: unsure
<222> LOCATION: (127)
<221> NAME/KEY: unsure
<222> LOCATION: (129)..(130)
<221> NAME/KEY: unsure
<222> LOCATION: (155)

<400> SEQUENCE: 6
accacagcag gttatggttc atacaggact taaatgacca gtgaatactg caaaaaaata    60
aagctattct gcaaaatctg tgtaaaaaca acgcgtagta tcagaataga acagttaaaa    120
cagaagncnn agcagttact gaagacagac ggcanacagg cagctgcgcc acagggttga    180
gcgtcccata gccatgtaca gcgtctaagg gaccgagt    218

<210> SEQ ID NO 7
<211> LENGTH: 526
<212> TYPE: DNA
<213> ORGANISM: Homo sapiens

<400> SEQUENCE: 7
actgaataca gtagacaact gtaacacata tggtattatg tgtatcttac catatacaaa    60
ggtaaagtgt tctgccacaa tatcatgagc tttacaacgg ggtatgactt cattaggcca    120 taggagttttt cagcttcatt ataatcttat agaaccacgg atggtatatg cagcctactg    180
ctgatcacgt tggtatacag acacgtattc ccttctccca cacggcctgt tactagccac    240
gagtgggtga ttggctgaga gtaatgcact gtaggcagtt gtggctactt ttacgagaac    300
tgtcttgtca ggggagatgt atttaaacca gggacagatg ggccacagga gaaacataac    360
agctatggct gaaattcatg tgtattctac aattgccatg ccatttaat tcaataaata    420 tgtgagtttt tttatcatct gccaagcatt gttcataatt aacaggacaa aaacccaaac    480
ttttgccttt ttggagccta cagtctagaa taaggagaga aacaaa    526

<210> SEQ ID NO 8
<211> LENGTH: 276
<212> TYPE: DNA
<213> ORGANISM: Homo sapiens
<220> FEATURE:
<221> NAME/KEY: unsure
<222> LOCATION: (96)
<221> NAME/KEY: unsure
<222> LOCATION: (113)..(114)
<221> NAME/KEY: unsure
<222> LOCATION: (132)
<221> NAME/KEY: unsure
<222> LOCATION: (171)
<221> NAME/KEY: unsure
<222> LOCATION: (180)..(181)
<221> NAME/KEY: unsure
<222> LOCATION: (207)
<221> NAME/KEY: unsure
<222> LOCATION: (235)
<221> NAME/KEY: unsure
<222> LOCATION: (239)
<221> NAME/KEY: unsure
<222> LOCATION: (257)
<221> NAME/KEY: unsure
<222> LOCATION: (259)

<400> SEQUENCE: 8

```
aaaaaaagga ggaggagaaa atggaagtgg atgaggcagg caaaaaggag gaaaaagaga      60
ggaaaaagag aaccgttgga gccaaactta ccaggnttca ttagatacac ccnnagcccg     120
agttatgcct angcccagct taagcgtaca ctaaccatag ccgtgagacc ntagtagatn    180
naccacgcct ttcaagaaca cactcantct attgtgagcg cccatcactc caatntccnt    240
ggacacgggc acttacncna gcttgcacat gaacaa                              276
```

<210> SEQ ID NO 9
<211> LENGTH: 662
<212> TYPE: DNA
<213> ORGANISM: Homo sapiens

<400> SEQUENCE: 9

```
actagaacgt gaagcacctt tatttagcaa ctaattacaa cagagttgct taagattgat    60
gcagactaaa ctcattcatg acaactagca acaacgatta ctgacactac acttagctaa   120
gcttccattc acttcacgcg aatcttactg cccaacagca tcacacatta tccctgaaa    180 ctctccactc ttctcctcct gacctatgaa gcatcacaac actgacggca tcaaccaagc   240
tgcgcctaac ttctccttca gcgcgcttct gcctatctaa cacgacttct aacactgacc   300
gcatgactac ctctgctaca acgatactcg taacaaacga acgcgccctg gaccattaac   360
ttattcacag ttctcccaac tctgaccacc tcttccctac cctctctcac acgcggaacc   420
cctctgatac acctaaatac cgctccacgc gggcgcgcgc taaacccact cactggccac   480
caatcaacaa accactccta aacacttacc agcacttcct ccacgctaca cagtgtcccc   540
aaaagataac agcccaaact ccctgcctac actgctcact actacacaca ccccacccaa   600
caccaccaca cacaaccccc caccacaccc ctaccgccac aaacacaaca ccgcccaacc   660
ac                                                                   662
```

<210> SEQ ID NO 10
<211> LENGTH: 620
<212> TYPE: DNA
<213> ORGANISM: Homo sapiens
<220> FEATURE:
<221> NAME/KEY: unsure
<222> LOCATION: (195)

<400> SEQUENCE: 10

```
acacatttag gtaatctctg tgttccccag cccctctaaa gagcatcact gtgtcctcct     60
tgcctatatc catgccctct gtcaggaaag gccttgccct tttcctctat gccaactccc    120
cactgtccct cctgatacat ctccaatatt acctcttctc caacctccct gggagagtta    180
attacctcct ccttngggct cctataacaa cttttacatc tcttgcaaga ggttacttga    240
attacttgtt tacatacatg tctatctccc aaacaagtct aaaaatggta ggcttctaaa    300
taattatacg tttgataaat atgaatgaat gaccttttct atggaaagct aggcgctaaa    360
ggtgatagag agataacatg cacatacgag ctctcaaggg aaatagacag acacatagat    420
aatgtataag tagaataata attctttgaa ttgaaatccc cagggaaaca ttttcactca    480
accgaaaatc taactgcaat ctaaagattt tcacatacaa ccacttggca ttgacttaca    540 actcccaccta gataggttca taagtcaga tccttttctt gttacattct tagagctcat    600
aaaggtggcc tgaacaggca                                                620
```

<210> SEQ ID NO 11
<211> LENGTH: 486

<212> TYPE: DNA
<213> ORGANISM: Homo sapiens

<400> SEQUENCE: 11

| | | | | | |
|---|---|---|---|---|---|
| ggcgcctgga | gctgcgtgag | acgccgtcat | tctcccacac | cctgggagca | gtggggaacc | 60 |
| ctgtatgcga | cttcacagca | caccacgctc | cgtgtgagct | attaaaggcc | caccacgcat | 120 |
| cctcgtcttt | cagtgacact | ttcctgaaga | aataatacaa | tctggaatgg | gctacagaat | 180 |
| ctatccccta | gggtgagtga | caggaggggg | atgggtgaaa | caaagtcaca | tggctgtaag | 240 |
| cagctatcta | ctgaagcagg | atggttacct | ttctctactt | ttatgcttga | aatttctcac | 300 |
| aaataaagat | gagaaaatac | aaaaaaaaaa | aaaaaaaaa | cacacacaaa | aaacgccggg | 360 |
| ggaacaccgg | gccctacggg | tgcccgtgt | gaacatggga | tacgggccca | acaacccgag | 420 |
| aaaaatagca | cacacagaga | gagaaagaga | ccgacgcaga | accgacgacg | acgcagagac | 480 |
| agacag | | | | | | 486 |

<210> SEQ ID NO 12
<211> LENGTH: 322
<212> TYPE: DNA
<213> ORGANISM: Homo sapiens

<400> SEQUENCE: 12

| | | | | | |
|---|---|---|---|---|---|
| actacatttc | caaccctgag | atggagtgtt | ataggagcag | ggaaatcagc | cacgggtggg | 60 |
| tgtgggcagg | aatggttaaa | cactactgtt | atttcagtaa | tgtgataatt | ggagttttaa | 120 |
| gggtatgtgt | gtgtgttttg | ggaaagtaga | gtggagcagg | agaaagggta | tgtagacaac | 180 |
| tgtgttagag | aaattgaatc | tcagatggtg | agtgtttat | tttcccacct | tactcttgct | 240 |
| tctttaagtt | actactccca | caggagattg | gctatagact | gacatgagtg | agtaaagtta | 300 |
| ctcattaggg | gaatctaagc | tt | | | | 322 |

<210> SEQ ID NO 13
<211> LENGTH: 519
<212> TYPE: DNA
<213> ORGANISM: Homo sapiens
<220> FEATURE:
<221> NAME/KEY: unsure
<222> LOCATION: (146)
<221> NAME/KEY: unsure
<222> LOCATION: (322)

<400> SEQUENCE: 13

| | | | | | |
|---|---|---|---|---|---|
| acgactaata | tcttcaattt | actaagaaga | taaagaggtc | gataaataag | gaggtcaagc | 60 |
| ccgcttttgc | aacggtcaca | cacggaaaga | aagcagaacc | acgaaaactg | acacttcgcg | 120 |
| ctgctcaccc | tgcggcgtgg | gcgcanctag | aaggtctctt | tgacactccc | ttcggcctac | 180 |
| cgctcgaccg | cgattctcga | ctgtgcacat | cttattctgc | gccctgcagc | gcgagctaca | 240 |
| cgcacaggtt | cggtattttc | catttagctc | acggacagga | cgcttgcgtg | cttgaaggct | 300 |
| tacgcactac | agcttactca | anggcaacac | gcataaccta | accaatgaga | ctcccgcaag | 360 |
| ctttatgccc | aaaaaccctc | gcgactgcgt | atgccattc | catggccagc | gacgctctag | 420 |
| gcgataactc | cactactgcg | actgctagca | cttccgtgac | taatcccctg | gcggcgttgc | 480 |
| aagcatttgt | cataagcttt | ccgtgtgcgc | tgactcaaa | | | 519 |

<210> SEQ ID NO 14
<211> LENGTH: 248
<212> TYPE: DNA
<213> ORGANISM: Homo sapiens

```
<400> SEQUENCE: 14
acttccagcc tccagaaatg agaaagaata attttttttg tttcagccac ccagtcatat     60
tagctgtggc agcctgaggt gactaatatc ctgccaaaaa cgcacagcca aacaccaggc    120
agacccaaac tgagggatcg tgagaataga tctggcctat aatcagaagt gtcgaggtca    180
tgaacgtcaa gggaagattg aggaaccatt ccagacaaat gtaattaggc acactctcac    240
acaagctt                                                             248

<210> SEQ ID NO 15
<211> LENGTH: 473
<212> TYPE: DNA
<213> ORGANISM: Homo sapiens

<400> SEQUENCE: 15
actcctatct aaatgttgtc tctctcattg atgggcctga aaaaaaacaa acatttttta     60
aaatggtata gccacattgg caactttcta aaagtcctaa ttttttctag acaaattgat    120
aatttatgct acttattttt agtgtaacat ttcctcaaat gattaaaatg aaatctaaac    180
tattttcatc agttttactt ccaattattc tttcttttgc tctattattt cttagagttg    240
tcaagggcaa attaattagc agctgttttt attaagaaga attctgattt ctcctaataa    300
gtgatggcag ctttataatt aatattttaa cctgcctgct gacctactaa ttagaatagg    360
aaatggcttt tagacaggat cagttggcac tagacatcac cacgcactta cacacacatg    420
ctcaaatcaa ccttggggttg agagaacttt aggtgttagt ttatataaag ctt          473

<210> SEQ ID NO 16
<211> LENGTH: 394
<212> TYPE: DNA
<213> ORGANISM: Homo sapiens

<400> SEQUENCE: 16
acgttgacat gcactattgc acttgattct tgtaacaaat ttgtaagaaa acaagggtag     60
ctattattag tccctcttta tcattattat gaaaacattt ctaaatagaa aaattgagga    120
ccataaatgt atacggaaaa tttgttttta aagaaatac ccaagtgaaa gcacaatgtt     180
ctcaagatcc aggtcaagtt ttcttgtata gaaggaataa gtttaacata aaaaccataa    240
gtttctatga atatatcttg ttaataaatt taatgatgtg actaattccc aagctctatg    300
ttacttagag aactatactt aggatactgt gtattcatcc atacaataaa gttttttttac   360 ccaacgaaaa aaaaaaaaaa aaaaaaaag gctg                                 394

<210> SEQ ID NO 17
<211> LENGTH: 391
<212> TYPE: DNA
<213> ORGANISM: Homo sapiens

<400> SEQUENCE: 17
gaccaactgt gctccatctc cacgaggttg tgaagagaga aaatgggccg cctgcactac     60
agcatgagag ccatcagtta gacaaaaaga agcatggtga gacaggcaag gccctccaga    120
gaaagccagg aaggcagtga gtggctttca aaaccgatgt ggtgcattca gaggctggaa    180
gatggacaat attactttcc cagaaagttt cgcaaaactt tctcttttgt tggcatgttg    240
aaaatagcaa gccattgcct cttccccccgg ccgctgggtc tgctggcaag catgttaatt    300
tccagaactc acagaattaa agccagagag gatccttgta actcatcttc tctccctccc    360
```

| | |
|---|---|
| cagcctccca cagaaccata cccaaaagct t | 391 |

<210> SEQ ID NO 18
<211> LENGTH: 634
<212> TYPE: DNA
<213> ORGANISM: Homo sapiens

<400> SEQUENCE: 18

| | |
|---|---|
| acagtttgat tcttgtttgt ctaattttgt agtcaacagc cttctgattt tatagaattc | 60 |
| tctcttattt tgttctcatg agatctaaaa tcgtctgtgt aattggcttg tggtaaatat | 120 |
| ctcaaggag accaatggta aatatctcaa atgagagcat tagagatatt ttaacctctt | 180 |
| acaaagaggc taaaagcaac ttgtcctatt agaagtgtat cttaattaag tattgcttag | 240 |
| aaagtttcta agacatcatg attatactga agttagattc tggacaaagt gtatgagaaa | 300 |
| gtttacggct ataaaaggtt tgctgagagt ttttccttaa ataacgcatg catgaatctt | 360 |
| ttctttgtct atgaattttt aaagtattta tgggccctcc ggtctcttaa atttaaagtt | 420 |
| cattttcact ttctactctc ttctatttct aagacaaatc ttttcttct tacgtttttt | 480 |
| acttttcaaa gtttgggaaa aaatactgat ttttggaagc ctattttatt gccttctttc | 540 |
| atagccatct tgtgctcatt ttctgtccta atatttatcc cggacaattg gcttgggagc | 600 |
| caagcataat attttttgag gtcgccggat ccag | 634 |

<210> SEQ ID NO 19
<211> LENGTH: 239
<212> TYPE: DNA
<213> ORGANISM: Homo sapiens

<400> SEQUENCE: 19

| | |
|---|---|
| actagagagc attattcctg attaagtgtt aagaaaagtt ttattaataa cattaattct | 60 |
| ctagataatc acttttttata tcctttcaag atgtctctat cttgaaacat ttatctgcca | 120 |
| cattataaaa atagatatta ttttattcag tttatagaat actcactgtg tttaaggcac | 180 |
| tattctggac atcgagctgc aatagtgaac ataatcaagt ttctgctctc attaagctt | 239 |

<210> SEQ ID NO 20
<211> LENGTH: 515
<212> TYPE: DNA
<213> ORGANISM: Homo sapiens

<400> SEQUENCE: 20

| | |
|---|---|
| actaccccca tgaagtaggt taattaagaa gacaaatgat cagaaaagta gtgagaaaac | 60 |
| tgaaaaatcc taatgccttg taagtcagta ttagaaaact ttaagaacta agatttcagc | 120 |
| ctgaggaagc tgattaaaaa ataaaaataa aaaaccacac caagattgat ggcaatagat | 180 |
| gtaattgaaa agaggaaaca gaactgagga atgattttttg aatttgagta ggaggaggtc | 240 |
| attggtattt ttagaagggt ttctgtggaa tacagaaaca agaaatcatg ttacagagtg | 300 |
| tatataggag gggaaagtat ttaaaaagca cagtcaaggg atacagggca ctcttgaaaa | 360 |
| ttttaacaat taaatgaggt ggcagtagaa aaaaaaaaa aaaaaaaaac aaaaaaaccc | 420 |
| gggggcgaaa cacgggccaa aggggtaccc gggggacaac cggaaccccg gcacccaaaa | 480 |
| ataatctcaa cccacaacact cccgacaaac cacct | 515 |

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 21
ccatcgtctt cctttatcca act                                          23

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 22
tgggtgattt cagagaactg ct                                           22

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 23
tcaattatag gcaaaggaac tcacagaaga aaac                              34

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 24
gtggctcttt cttttccctc ag                                           22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 25
cgcagagaga caacccaaga                                              20

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 26
acctgctgtt gctcctggct agtcttg                                      27

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 27
tccatctcca cgaggttgtg                                              20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 28
gccttgcctg tctcaccat                                               19

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 29
tgtctaactg atggctctca tgctgtagtg                                   30

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 30
agaggctaaa agcaacttgt cc                                           22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 31
ggaaaaactc tcagcaaacc tt                                           22

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 32
agccgtaaac tttctcatac actttgtcca                                   30

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 33
gcagcctgag gtgactaata tcc                                          23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic

```
<400> SEQUENCE: 34
gcttgtgtga gagtgtgcct aat                                         23

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 35
ttccaattat tctttctttt gctc                                        24
```